US008804121B2

(12) United States Patent
Sugiyama et al.

(10) Patent No.: US 8,804,121 B2
(45) Date of Patent: Aug. 12, 2014

(54) CELL OBSERVATION DEVICE AND CELL OBSERVATION METHOD

(75) Inventors: Norikazu Sugiyama, Hamamatsu (JP); Takuji Kataoka, Hamamatsu (JP); Takahiro Ikeda, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 105 days.

(21) Appl. No.: 13/642,012

(22) PCT Filed: Apr. 13, 2011

(86) PCT No.: PCT/JP2011/059208
§ 371 (c)(1),
(2), (4) Date: Jan. 3, 2013

(87) PCT Pub. No.: WO2011/132587
PCT Pub. Date: Oct. 27, 2011

(65) Prior Publication Data
US 2013/0288286 A1 Oct. 31, 2013

(30) Foreign Application Priority Data
Apr. 23, 2010 (JP) ................................. 2010-100292

(51) Int. Cl.
*G01N 21/55* (2014.01)
(52) U.S. Cl.
USPC ....................................................... 356/341
(58) Field of Classification Search
USPC ....................................................... 356/925
See application file for complete search history.

(56) References Cited

U.S. PATENT DOCUMENTS

| 5,162,990 A | 11/1992 | Odeyale et al. |
| 2003/0112444 A1 | 6/2003 | Yang et al. |
| 2010/0094135 A1* | 4/2010 | Fang-Yen et al. ............. 600/476 |

FOREIGN PATENT DOCUMENTS

| JP | 2003-98439 | 4/2003 |
| JP | 2004-529360 | 9/2004 |

(Continued)

OTHER PUBLICATIONS

C. K. Choi et al., "Multicontrast microscopy technique to dynamically fingerprint live-cell focal contacts during exposure and replacement of a cytotoxic medium", Journal of Biomedical Optics, Sep./Oct. 2008, vol. 13(5), pp. 0540691-1-054069-5.
I. Weber et al., "Image processing for combined bright-field and reflection interference contrast video microscopy", Computer Methods and Programs in Biomedicine, 1997, vol. 53, pp. 113-118.

(Continued)

*Primary Examiner* — Isam Alsomiri
*Assistant Examiner* — Vicente Rodriguez
(74) *Attorney, Agent, or Firm* — Drinker Biddle & Reath LLP

(57) ABSTRACT

A cell observation device is provided with a reflection interference measurement light source 106, a quantitative phase measurement light source 105, a reflection interference detection camera 110 which images light emitted from the reflection interference measurement light source 106 and reflected from cells 101, to generate a reflection interference image, a quantitative phase detection camera 112 which images light emitted from the quantitative phase measurement light source 105 and transmitted by the cells 101, to generate a quantitative phase image, an image alignment unit 201 which matches a spatial position of the reflection interference image with a spatial position of the quantitative phase image, to implement alignment between the two images, a first extraction unit 204 which extracts a first parameter from the reflection interference image in alignment with the quantitative phase image, and a second extraction unit 205 which extracts a second parameter from the quantitative phase image in alignment with the reflection interference image.

15 Claims, 34 Drawing Sheets

(56) References Cited

FOREIGN PATENT DOCUMENTS

| JP | 2005-326495 | 11/2005 |
|----|-------------|---------|
| JP | 2007-108448 | 4/2007 |
| JP | 2007-509314 | 4/2007 |
| JP | 2007-524075 | 8/2007 |
| JP | 2009-89629 | 4/2009 |
| JP | 2010-26392 | 2/2010 |
| WO | 2005/029413 | 3/2005 |
| WO | 2009/050886 | 4/2009 |

OTHER PUBLICATIONS

Y. Usson et al., "Quantitation of Cell-Matrix Adhesion Using Confocal Image Analysis of Focal Contact Associated Proteins and Interference Reflection Microscopy", Cytometry, 1997, vol. 28, pp. 298-304.

T. Yamauchi et al., "Label-free classification of living cells using low-coherent reflection-type quantitative phase microscopy", Optics & Photonics Japan Koen yoshishu, Nov. 8, 2010, vol. 2010, pp. 542-543, including English Abstract.

* cited by examiner

Fig.6

| | Parameter | Cell A | Cell B | Cell C | Cell D | Cell E | Cell F | Cell G | Cell H | Cell I | ... |
|---|---|---|---|---|---|---|---|---|---|---|---|
| Reflection interference | average luminosity | 19.62864 | -0.26801 | 8.112167 | 14.27295 | 35.52416 | 42.77409 | 45.27966 | 163.5286 | 151.4515 | |
| | standard deviation of luminosity | 1.174527 | 1.223651 | 1.509809 | 1.35426 | 3.08762 | 1.602223 | 2.765116 | 4.430906 | 1.182973 | |
| | texture analysis gray level histogram kurtosis | 10.81502 | 11.73744 | 8.594997 | 8.36697 | 7.565543 | 7.160647 | 8.763079 | 4.639712 | 3.282138 | |
| | texture analysis co-occurrence matrix energy | 0.201982 | 0.251122 | 0.223359 | 0.19228 | 0.155856 | 0.211896 | 0.114241 | 0.071744 | 0.116483 | |
| Quantitative phase | average optical thickness (nm) | 208.7405 | 187.324 | 160.3147 | 209.0842 | 229.1418 | 161.2536 | 159.2455 | 99.84034 | 115.7943 | |
| | standard deviation of optical thickness | 8.424104 | 13.80244 | 9.779022 | 13.87463 | 8.583759 | 5.401401 | 8.861581 | 5.787113 | 4.224522 | |

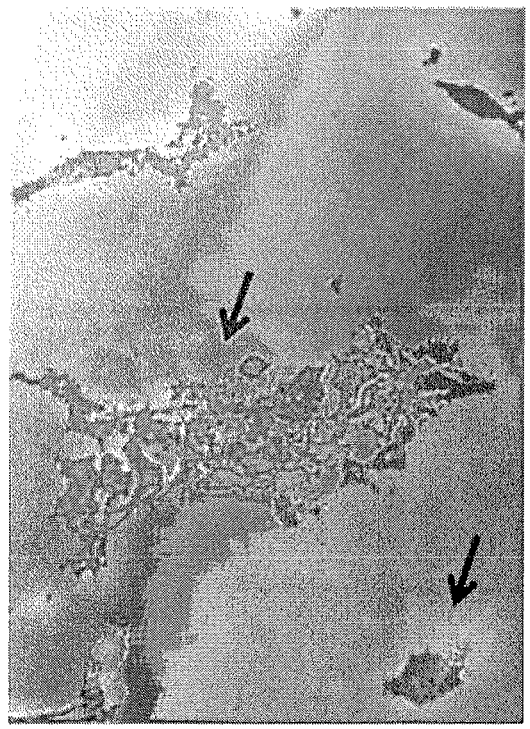
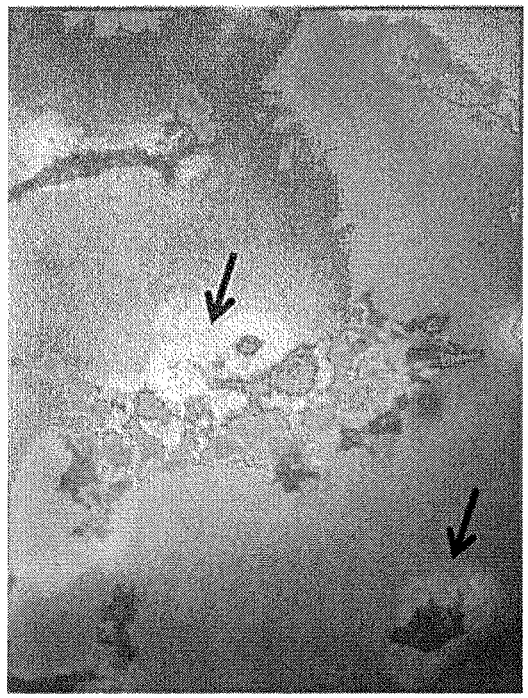
Fig.11

*Fig.14*
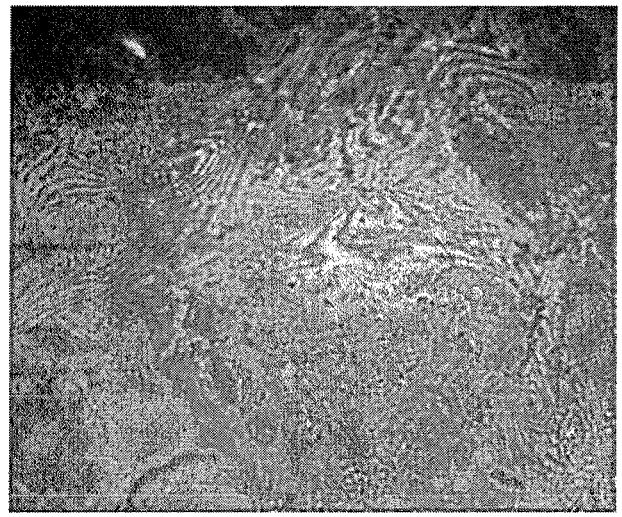
BOTTOM OF VESSEL WITH ANTIREFLECTION COAT
UNTREATED Fig. 15
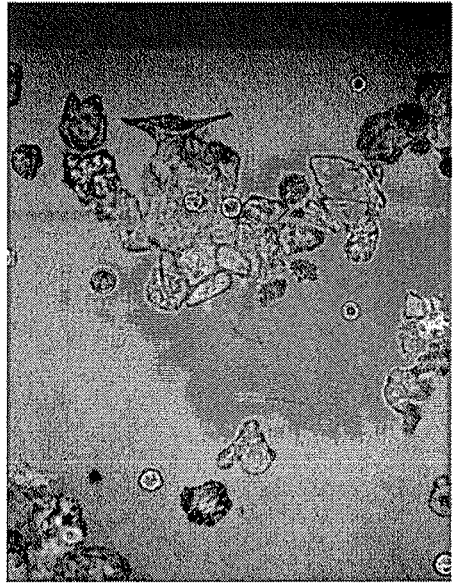
(B)
TOP OF VESSEL WITH ANTIREFLECTION COAT
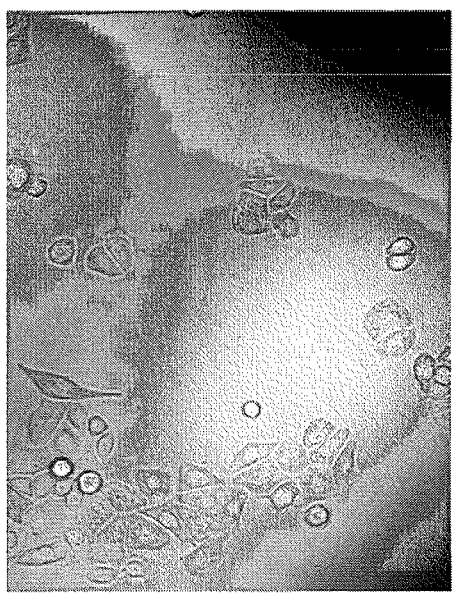
(A)
TOP OF VESSEL UNTREATED

Fig.28

| | QUANTITATIVE PHASE IMAGE | | REFLECTION INTERFERENCE IMAGE | | | | |
|---|---|---|---|---|---|---|---|
| | area (μm²) | optical thickness (nm) | co-occurrence matrix local uniformity | co-occurrence matrix inertia | gray level histogram skewness | gray level histogram kurtosis | gray level histogram √(variance)/average |
| INS-1 | 99.01 | 162.48 | 0.539 | 0.629 | 0.801 | 3.041 | 0.0317 |
| INS-1 | 78.63 | 135.91 | 0.663 | 1.891 | 0.566 | 2.487 | 0.0332 |
| INS-1 | 92.46 | 120.59 | 0.637 | 0.967 | 0.627 | 2.611 | 0.0321 |
| INS-1 | 96.93 | 140.24 | 0.707 | 1.147 | 0.448 | 2.335 | 0.0321 |
| INS-1 | 113.26 | 121.12 | 0.494 | 0.813 | 0.445 | 2.373 | 0.0322 |
| INS-1 | 79.98 | 140.15 | 0.627 | 2.124 | 0.474 | 2.374 | 0.0321 |
| INS-1 | 95.48 | 131.13 | 0.623 | 1.262 | 0.432 | 2.339 | 0.0317 |
| INS-1 | 105.77 | 139.78 | 0.606 | 1.163 | 0.476 | 2.401 | 0.0316 |
| INS-1 | 80.19 | 158.98 | 0.620 | 1.546 | 0.445 | 2.350 | 0.0314 |
| INS-1 | 170.67 | 119.34 | 0.628 | 1.234 | 0.450 | 2.361 | 0.0311 |
| MIN6 | 401.46 | 74.57 | 0.744 | 0.757 | 0.863 | 3.366 | 0.0259 |
| MIN6 | 270.73 | 85.98 | 0.805 | 0.447 | 0.889 | 3.871 | 0.0252 |
| MIN6 | 271.66 | 83.35 | 0.767 | 0.628 | 0.835 | 3.735 | 0.0249 |
| HeLa | 792.22 | 151.81 | 0.574 | 1.759 | -0.067 | 3.045 | 0.0383 |
| HeLa | 759.77 | 171.74 | 0.540 | 2.096 | -0.044 | 3.001 | 0.0389 |
| HeLa | 342.39 | 143.21 | 0.568 | 1.792 | -0.025 | 2.945 | 0.0393 |
| unknown | 479.47 | 238.24 | 0.767 | 2.903 | 0.950 | 3.952 | 0.0340 |
| unknown | 666.89 | 162.81 | 0.599 | 2.560 | 0.953 | 3.871 | 0.0365 |
| unknown | 643.69 | 128.07 | 0.705 | 1.414 | 0.914 | 3.804 | 0.0360 |
| number of samples | 43 | 43 | 43 | 43 | 43 | 43 | 43 |
| average | 402.33 | 144.20 | 0.660 | 1.258 | 0.553 | 3.221 | 0.0325 |
| standard deviation | 228.00 | 43.90 | 0.080 | 0.584 | 0.378 | 0.606 | 0.0045 |

Fig.29

| | QUANTITATIVE PHASE IMAGE | | REFLECTION INTERFERENCE IMAGE | | | | |
|---|---|---|---|---|---|---|---|
| | area (μm²) | optical thickness (nm) | co-occurrence matrix local uniformity | co-occurrence matrix inertia | gray level histogram skewness | gray level histogram kurtosis | gray level histogram √(variance)/average |
| information amount | 2155199.7 | 82865.6 | 0.276 | 14.656 | 6.134 | 15.785 | 0.0008738 |

Fig.30

| | QUANTITATIVE PHASE IMAGE | | | REFLECTION INTERFERENCE IMAGE | | | | |
|---|---|---|---|---|---|---|---|---|
| | area (μm²) | optical thickness (nm) | co-occurrence matrix local uniformity | co-occurrence matrix inertia | gray level histogram skewness | gray level histogram kurtosis | gray level histogram √(variance)/average |
| INS-1 | -1.367 | 0.416 | -1.508 | -1.078 | 0.655 | -0.296 | -0.172 |
| INS-1 | -1.456 | -0.189 | 0.040 | 1.083 | 0.035 | -1.210 | 0.151 |
| INS-1 | -1.396 | -0.538 | -0.286 | -0.499 | 0.195 | -1.006 | -0.082 |
| INS-1 | -1.376 | -0.090 | 0.584 | -0.190 | -0.280 | -1.461 | -0.080 |
| INS-1 | -1.304 | -0.526 | -2.076 | -0.763 | -0.287 | -1.399 | -0.062 |
| INS-1 | -1.450 | -0.092 | -0.409 | 1.483 | -0.210 | -1.397 | -0.096 |
| INS-1 | -1.382 | -0.298 | -0.469 | 0.007 | -0.322 | -1.455 | -0.185 |
| INS-1 | -1.337 | -0.101 | -0.675 | -0.163 | -0.205 | -1.352 | -0.209 |
| INS-1 | -1.450 | 0.337 | -0.499 | 0.493 | -0.288 | -1.437 | -0.240 |
| INS-1 | -1.053 | -0.566 | -0.405 | -0.042 | -0.273 | -1.419 | -0.321 |
| MIN6 | -0.040 | -1.586 | 1.040 | -0.858 | 0.821 | 0.240 | -1.471 |
| MIN6 | -0.614 | -1.326 | 1.810 | -1.389 | 0.890 | 1.074 | -1.623 |
| MIN6 | -0.610 | -1.386 | 1.333 | -1.079 | 0.745 | 0.849 | -1.685 |
| HeLa | 1.673 | 0.173 | -1.080 | 0.857 | -1.644 | -0.290 | 1.284 |
| HeLa | 1.531 | 0.627 | -1.504 | 1.464 | -1.581 | -0.362 | 1.429 |
| HeLa | -0.300 | -0.023 | -1.145 | 0.914 | -1.532 | -0.455 | 1.516 |
| unknown | 0.302 | 2.142 | 1.328 | 2.818 | 1.050 | 1.208 | 0.326 |
| unknown | 1.124 | 0.424 | -0.766 | 2.229 | 1.059 | 1.074 | 0.880 |
| unknown | 1.022 | -0.368 | 0.559 | 0.267 | 0.954 | 0.963 | 0.782 |
| number of samples | 43 | 43 | 43 | 43 | 43 | 43 | 43 |
| average | 0 | 0 | 0 | 0 | 0 | 0 | 0 |
| standard deviation | 1 | 1 | 1 | 1 | 1 | 1 | 1 |
| information amount | 43 | 43 | 43 | 43 | 43 | 43 | 43 |

Fig.31

| | QUANTITATIVE PHASE IMAGE | | REFLECTION INTERFERENCE IMAGE | | | | |
|---|---|---|---|---|---|---|---|
| | X1 | X2 | X3 | X4 | X5 | X6 | X7 |
| | area (μm²) | optical thickness (nm) | co-occurrence matrix local uniformity | co-occurrence matrix inertia | gray level histogram skewness | gray level histogram kurtosis | gray level histogram √(variance)/average |
| | a1 | a2 | a3 | a4 | a5 | a6 | a7 |
| coefficients of f | -0.0543 | -0.2477 | 0.4583 | -0.4003 | 0.4588 | 0.3176 | -0.5041 |

Fig.32

| | QUANTITATIVE PHASE IMAGE | | REFLECTION INTERFERENCE IMAGE | | | | |
|---|---|---|---|---|---|---|---|
| | X1 | X2 | X3 | X4 | X5 | X6 | X7 |
| | area (μm²) | optical thickness (nm) | co-occurrence matrix local uniformity | co-occurrence matrix inertia | gray level histogram skewness | gray level histogram kurtosis | gray level histogram √(variance)/average |
| coefficients of g | b1 | b2 | b3 | b4 | b5 | b6 | b7 |
| | 0.5441 | 0.5944 | 0.2499 | 0.1715 | 0.2563 | 0.3833 | 0.2151 |

| | FIRST PRINCIPAL COMPONENT(f) | SECOND PRINCIPAL COMPONENT(g) |
|---|---|---|
| INS-1 | 0.0053 | -1.0544 |
| INS-1 | -0.7325 | -1.1460 |
| INS-1 | 0.0906 | -1.6034 |
| INS-1 | -0.1098 | -1.3518 |
| INS-1 | -0.9886 | -2.3080 |
| INS-1 | -1.1697 | -1.3162 |
| INS-1 | -0.5842 | -1.7392 |
| INS-1 | -0.5636 | -1.6130 |
| INS-1 | -0.8968 | -1.3190 |
| INS-1 | -0.3843 | -1.7110 |
| MIN6 | 2.4102 | -0.8663 |
| MIN6 | 3.3149 | -0.6238 |
| MIN6 | 2.8808 | -0.8598 |
| MIN6 | 2.7797 | -0.9338 |
| MIN6 | 2.9175 | -0.4560 |
| MIN6 | 3.1047 | -0.1283 |
| MIN6 | 1.9636 | -0.9889 |
| MIN6 | 1.7936 | -0.6305 |
| MIN6 | 1.9824 | 0.2060 |
| MIN6 | 2.2268 | 0.8942 |

(B)

| | FIRST PRINCIPAL COMPONENT(f) | SECOND PRINCIPAL COMPONENT(g) |
|---|---|---|
| MIA-PaCa | 0.460739 | -0.327086 |
| MIA-PaCa | 0.4733767 | -0.160074 |
| MIA-PaCa | 0.4962 | 0.7451 |
| MIA-PaCa | 1.0495 | 1.0762 |
| MIA-PaCa | 0.0590 | -0.1175 |
| MIA-PaCa | 1.1962 | 1.5641 |
| MIA-PaCa | 0.5022 | 2.5742 |
| MIA-PaCa | 0.2819 | 2.6972 |
| MIA-PaCa | 1.4218 | 2.7020 |
| MIA-PaCa | 0.0136 | 1.5468 |
| HeLa | -3.0896 | 0.0986 |
| HeLa | -1.5914 | -0.4903 |
| HeLa | -2.8384 | 0.8184 |
| HeLa | -2.3352 | 0.0519 |
| HeLa | -2.9811 | -0.3074 |
| HeLa | -2.0304 | 0.2248 |
| HeLa | -2.2572 | -0.4153 |
| HeLa | -2.4672 | 0.6509 |
| HeLa | -3.0641 | 0.8552 |
| HeLa | -2.4802 | -0.5497 |
| unknown | -0.3662 | 3.0576 |
| unknown | -1.0274 | 1.9380 |
| unknown | 0.5335 | 1.3154 |

CELL OBSERVATION DEVICE AND CELL OBSERVATION METHOD

TECHNICAL FIELD

The present invention relates to a cell observation device and a cell observation method.

BACKGROUND ART

Conventionally, a cell state was determined and evaluated by an invasive method, for example, by attaching a fluorescence label to cells. However, since such a method uses a toxic pigment for the cells or, fixes and treats the cells with a fixative solution, the cells cannot be reused after the treatment, and it is thus difficult to evaluate the cells in a natural state, to continue cultivation after evaluation, and to use the cells for transplantation. Therefore, it can be said that the cell state is preferably determined and evaluated by a non-invasive method. Patent Literature 1 and Non Patent Literatures 1 to 3 disclose determination and evaluation of cells by non-invasive methods.

CITATION LIST

Patent Literature

Patent Literature 1: International Publication WO2005/029413

Non Patent Literatures

Non Patent Literature 1: Y. Usson, A. Guignandon, N. Laroche, M-H. Lafage-Proust, L. Vico, "Quantitation of Cell-Matrix Adhesion Using Confocal Image Analysis of Focal Contact Associated Proteins and Interference Reflection Microscopy," Cytometry, 28, 298-304, (1997)

Non Patent Literature 2: C. K. Choi, C. H. Margraves, A. E. English, K. D. Kihm, "Multicontrast microscopy technique to dynamically fingerprint live-cell focal contacts during exposure and replacement of cytotxic medium," J. Biomedical Optics, 13 (5), (2008)

Non Patent Literature 3: I. Weber, R. Albrecht, "Image processing for combined bright-field and reflection interference contrast video microscopy," Computer Methods and Programs in Biomedicine, 53, 113-118, (1997)

SUMMARY OF INVENTION

Technical Problem

Patent Literature 1 discloses a method using a quantitative phase microscope, as one of methods for determining and evaluating the cell state by a non-invasive method. This method allows non-invasive determination and evaluation on the cell state using a difference in optical path length depending upon the presence/absence of cell. However, information obtained by this method is limited to only information based on the optical thickness, area, and volume of cell, and a change in refractive index in cell, which is not necessarily an amount of necessary information enough to appropriately determine and evaluate the cell state.

Non Patent Literatures 1 to 3 disclose methods using a reflection interference microscope, as another example of the non-invasive methods. These methods allow non-invasive determination and evaluation on the cell state by making use of a phenomenon in which a contrast of bright and dark patterns appears because of interference between reflected light from an interface between a substrate and a culture solution and reflected light from an interface between the culture solution and cell membranes, based on adhesion states of individual cells to the substrate. However, the information obtained by these methods is limited to only information based on the adhesion states of cells to the substrate, which is not necessarily an amount of necessary information enough to appropriately determine and evaluate the cell state.

As described above, the methods using either the quantitative phase microscope or the reflection interference microscope singly can obtain only the information based on the optical thickness, area, and volume of cell, and the change in refractive index in cell, or only the information based on the adhesion states of cells to the substrate. Such single information only cannot be an amount of necessary information enough to appropriately determine and evaluate the cell state. We found no literatures disclosing or suggesting combinational use of the quantitative phase microscope and the reflection interference microscope, and the combinational use of the two microscopes must require some devising because the two microscopes are separate microscopes with different functions.

The present invention has been accomplished in view of the above circumstances and it is an object of the present invention to provide a cell observation device and a cell observation method enabling acquisition of a greater amount of information for appropriate determination and evaluation on the cell state.

Solution to Problem

In order to solve the above problem, a cell observation device of the present invention is one comprising: a reflection interference measurement light source; a quantitative phase measurement light source; reflection interference imaging means which images light emitted from the reflection interference measurement light source and reflected from a cell, to generate a reflection interference image; quantitative phase imaging means which images light emitted from the quantitative phase measurement light source and transmitted by the cell, to generate a quantitative phase image; image alignment means which matches a spatial position of the reflection interference image with a spatial position of the quantitative phase image, thereby to implement alignment between the two images; first extraction means which extracts a first parameter from the reflection interference image in the alignment with the quantitative phase image by the image alignment means; and second extraction means which extracts a second parameter from the quantitative phase image in the alignment with the reflection interference image by the image alignment means.

A cell observation method of the present invention is one comprising: a reflection interference imaging step wherein reflection interference imaging means images light emitted from a reflection interference measurement light source and reflected from a cell, to generate a reflection interference image; a quantitative phase imaging step wherein quantitative phase imaging means images light emitted from a quantitative phase measurement light source and transmitted by the cell, to generate a quantitative phase image; an image alignment step wherein image alignment means matches a spatial position of the reflection interference image with a spatial position of the quantitative phase image, thereby to implement alignment between the two images; a first extraction step wherein first extraction means extracts a first parameter from the reflection interference image in the alignment with the quantitative phase image by the image alignment means; and a second extraction step wherein second extraction means extracts a second parameter from the quantitative phase image in the alignment with the reflection interference image by the image alignment means.

The cell observation device and the cell observation method of the present invention as described above, comprise the reflection interference measurement light source, the reflection interference imaging means, and the first extraction means (which will be referred to hereinafter as "reflection interference measurement unit"), whereby the first parameter is obtained based on the reflected light from the cell. Furthermore, the device and method comprise the quantitative phase measurement light source, the quantitative phase imaging means, and the second extraction means (which will be referred to hereinafter as "quantitative phase measurement unit"), whereby the second parameter is obtained based on the transmitted light from the cell. In this manner, the cell observation device and the cell observation method of the present invention can obtain both of the first parameter and the second parameter by comprising both of the reflection interference measurement unit and the quantitative phase measurement unit, whereby a user obtains a greater amount of information for appropriately determining and evaluating a state of the cell. Furthermore, the first parameter is a parameter extracted from the reflection interference image in the alignment with the quantitative phase image and the second parameter is a parameter extracted from the quantitative phase image in the alignment with the reflection interference image; therefore, it can be said that the two parameters have consistency as to a location where the parameters are extracted in the cell. Namely, the alignment between the two images by the image alignment means of the present invention enables the two parameters to be utilized as parameters for determining and evaluating the state at the same location of the cell.

In the present invention, the device may further comprise: contour extraction means which extracts a contour of the cell, based on the quantitative phase image; contour application means which applies the contour extracted by the contour extraction means, to the reflection interference image to generate a reflection interference image after contour application; and third extraction means which extracts a third parameter from the reflection interference image after contour application.

In the present invention, the method may further comprise: a contour extraction step wherein contour extraction means extracts a contour of the cell, based on the quantitative phase image; a contour application step wherein contour application means applies the contour extracted by the contour extraction means, to the reflection interference image, to generate a reflection interference image after contour application; and a third extraction step wherein third extraction means extracts a third parameter from the reflection interference image after contour application.

According to this invention, the third parameter is further obtained in addition to the first parameter and the second parameter. Since this third parameter is a parameter obtained after matching of the cell contour between the quantitative phase image and the reflection interference image, it is different in property from the first parameter and the second parameter; when further obtaining this third parameter, the user obtains a greater amount of information for appropriately determining and evaluating the state of the cell.

There is no user's intervention in the process of extracting the contour of the cell from the quantitative phase image and applying the contour to the reflection interference image to generate the reflection interference image after contour application. On the other hand, the conventional method using the reflection interference microscope (which will be referred to hereinafter as "reflection interference method") requires preliminary recognition of the contour of each individual cell, and therefore the reflection interference method is often used in combination with another method for contour recognition. Non Patent Literature 1 above discloses the combination of the reflection interference method with the fluorescence method, but an operator defines cell contours by handwriting because it was difficult to automatically extract the cell contours. Non Patent Literature 2 discloses the combination of the reflection interference method with the transmission illumination method, but teaches nothing about automatic determination of cell contours without the aid of human hand. Furthermore, Non Patent Literature 3 discloses the combination of the reflection interference method with the bright-field method, and mentions automatization of extraction of cell contour, more or less; however, it describes, for example, that the user needs to manually set an optimum threshold for contour extraction while viewing a bright-field image, thereby admitting the necessity for user's intervention to some extent and thus failing in automatically determining the cell contours without the aid of human hand. In contrast to it, in the present invention, the processing including the cell contour extraction from the quantitative phase image, the contour application to the reflection interference image, and the generation of the reflection interference image after contour application is carried out by the contour extraction means and the contour application means, without the aid of human hand. When these processes are carried out without the aid of human hand, work efficiency is remarkably improved and in conjunction therewith an operation time is significantly reduced.

In the present invention, the first parameter may be information based on an adhesion state between a substrate on which the cell is laid, and the cell.

According to this invention, the obtained information based on the adhesion state of the cell to the substrate includes such information as an adhesion area of the cell to the substrate, a ratio of the adhesion area to an overall imaging range, and an adhesion condition (pattern or two-dimensional distribution) of the cell to the substrate, and the user is thus allowed to appropriately determine and evaluate the state of the cell, using these pieces of information.

In the present invention, the second parameter may be information based on an optical thickness, area, and/or volume of the cell, or a change in refractive index in the cell.

According to this invention, the obtained information includes information based on the optical thickness, area, and/or volume of the cell, or the change in refractive index in the cell, and the user is thus allowed to appropriately determine and evaluate the state of the cell, using these pieces of information.

In the present invention, the third parameter may be information based on the adhesion state to the substrate, in the contour of the cell.

According to this invention, the obtained information based on the adhesion state to the substrate in the contour of the cell, i.e., in the range of a space occupied by the cell is information such as a ratio of an adhesion area to an overall area of the cell, and the user is thus allowed to appropriately determine and evaluate the state of the cell, using such information.

In the present invention, the device may further comprise: reference storage means which stores as reference data a parameter preliminarily extracted for the cell of a known type or state; and analysis means which determines a type or state of an unknown cell, based on the reference data.

According to this invention, the type or state of the cell as an unknown specimen can be determined based on the reference data.

In the present invention, the device may further comprise analysis means which selects a predetermined parameter from parameters extracted for an unknown cell and which determines a type or state of the unknown cell, using the predetermined parameter selected.

According to this invention, the analysis means can perform processing, without depending on the reference data. This configuration can be realized without the reference storage means and thus the device configuration becomes simpler. The analysis means may be configured to automatically select a parameter indicative of a peculiar value as the predetermined parameter, or may be configured to select the predetermined parameter, based on an input from the user.

In the present invention, the device may further comprise: analysis means which, when the first extraction means or the second extraction means extracts three or more parameters, performs a principal component analysis on the three or more parameters, thereby to determine a type or state of an unknown cell.

According to this invention, the principal component analysis is carried out on the large number of extracted parameters, whereby the large number of parameters can be made to suitably affect the cell determination. The reason for it is that the principal component analysis is to perform the cell determination with two principal components suitably reflecting all of the large number of parameters or some of the three or more parameters, instead of selecting two out of the large number of extracted parameters.

In the present invention, low-coherent light may be used as the quantitative phase measurement light source.

According to this invention, the low-coherent light with a wide wavelength band and with low coherency is used in the quantitative phase measurement. This reduces interference noise originating in an optical system and thus allows stabler measurement.

In the present invention, low-coherent light may be used as the reflection interference measurement light source.

According to this invention, the low-coherent light with a wide wavelength band and with low coherency is used in the reflection interference measurement. When the illumination light used is one with a wide wavelength band, the distance of occurrence of interference can be decreased and the reflection interference image can be taken as being limited to an adhesion face of the cell to the substrate.

In the present invention, the device may further comprise: an objective lens which condenses the light emitted from the reflection interference measurement light source and reflected from the cell; and a slit of a ring shape at a position conjugate with an aperture stop on the reflection interference measurement light source side of the objective lens.

According to this invention, the illumination light from the reflection interference measurement light source passes through the slit opening in the ring shape, and the illumination light passes through the periphery without passing through the center of the objective lens, to illuminate the cell; therefore, the cell is illuminated with only the angled light with high NA, which can reduce influence of reflected light from a solution above the cell. The use of the slit of the ring shape can also reduce background light due to reflection inside the objective lens.

In the present invention, the device may further comprise a vessel which houses the cell, and an antireflection coat may be laid on the side of the vessel opposite to an adhesion face of the cell.

According to this invention, the reflection interference image of the cell adhesion face can be obtained with high contrast even in the case using the objective lens of a dry type.

In the present invention, the device may comprise an observation window at such a height as to contact a culture solution in which the cell is immersed, in an upper part of the vessel.

According to this invention, the height of the culture solution is kept constant with the use of the observation window, whereby the quantitative phase measurement can be carried out under a stable condition.

In the present invention, the observation window may be provided with an antireflection coat on the side thereof opposite to a surface in contact with the culture solution.

According to this invention, the reflection interference image of the cell adhesion face can be obtained with high contrast, while suppressing influence of reflected light from a top surface of the vessel.

In the present invention, the device may further comprise a mirror located between the reflection interference measurement light source and the reflection interference imaging means and between the quantitative phase measurement light source and the reflection interference imaging means and having variable ratios of reflection to transmission depending upon wavelengths.

According to this invention, the device comprises the mirror having the variable ratios of reflection to transmission depending upon wavelengths, whereby, for example, when the wavelengths of the quantitative phase measurement light source are different from those of the reflection interference measurement light source, the device can be configured to set such a ratio of reflection to transmittance as to make the mirror function as a half mirror for the wavelengths of the reflection interference measurement light source and to increase the transmittance according to the wavelengths of the quantitative phase measurement light source. This configuration allows the mirror to function as a half mirror in the reflection interference measurement and to reduce a loss of observation light in the quantitative phase measurement.

Advantageous Effect of Invention

The present invention can provide the cell observation device and the cell observation method capable of obtaining the greater amount of information for appropriately determining and evaluating the cell state.

BRIEF DESCRIPTION OF DRAWINGS

FIG. 6 is a drawing showing an example of parameters obtained from cells.

FIG. 11 is a drawing for showing an effect by the fourth example.

FIG. 14 is a drawing for showing an effect by the fifth example.

FIG. 15 is a drawing for showing an effect by the fifth example.

FIG. 28 is a drawing showing actually measured values of seven extracted parameters, in the sixteenth example.

FIG. 29 is a drawing showing the result of calculation of the sum of squares of deviations from a population as an information amount of parameters, in the sixteenth example.

FIG. 30 is a drawing showing the result of standardization for each of parameters, in the sixteenth example.

FIG. 31 is a drawing showing the result of calculation of coefficients for a first principal component f, in the sixteenth example.

FIG. 32 is a drawing showing the result of calculation of coefficients for a second principal component g, in the sixteenth example.

FIG. 33 is a drawing showing the result of calculation of the first principal component f and the second principal component g for each of cells, in the sixteenth example.

DESCRIPTION OF EMBODIMENTS

The preferred embodiments of the cell observation device and the cell observation method according to the present invention will be described below in detail with reference to the accompanying drawings. The cell observation device and the cell observation method will be first generally outlined and then they will be described in more detail using the sections of first to sixteenth examples. In the description of the drawings the same elements will be denoted by the same reference signs, without redundant description.

[Overall Configuration of Cell Observation Device 1]

Figure 1:
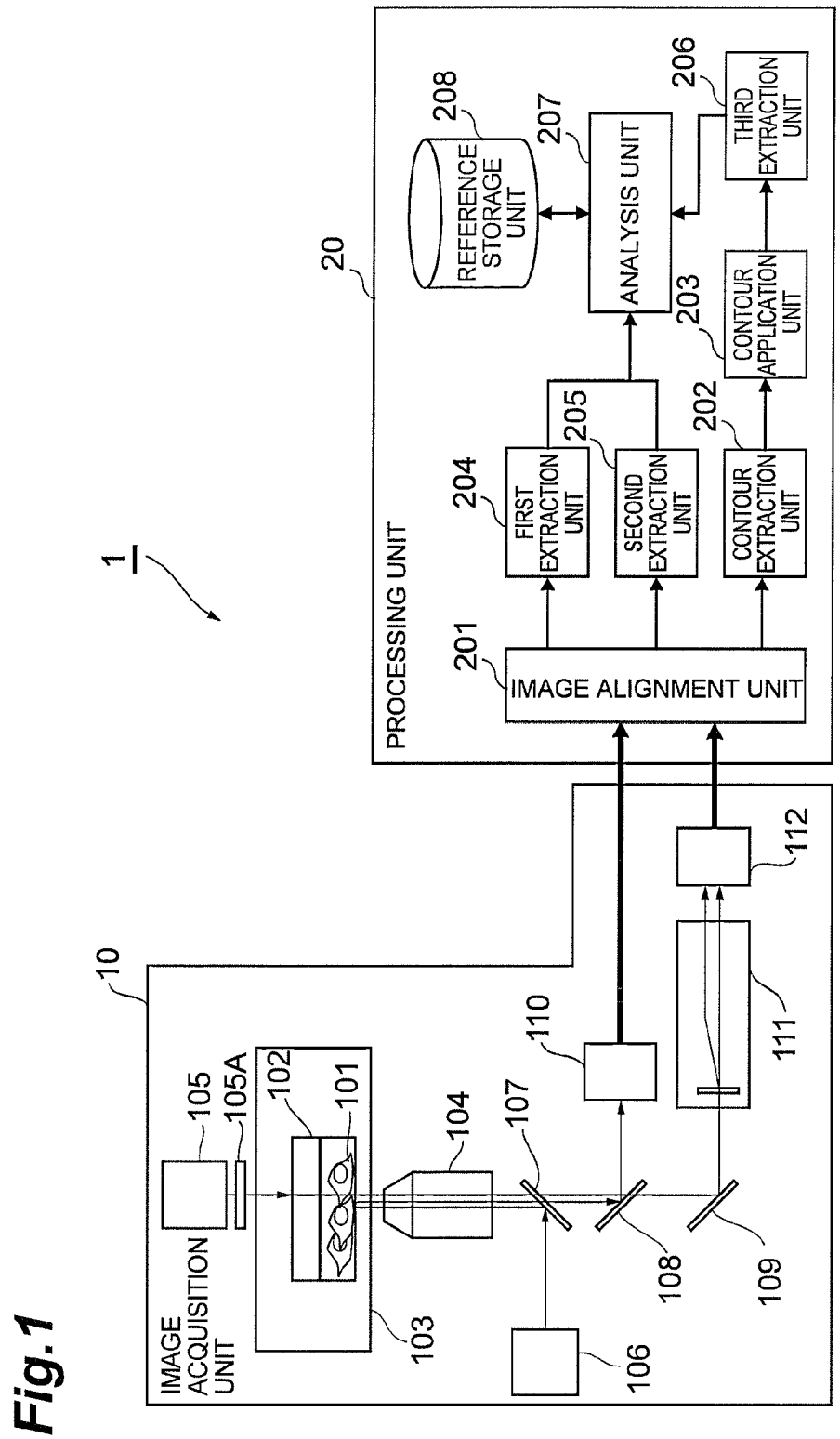
FIG. 1 is a schematic view showing an overall configuration of a cell observation device 1.

First, an overall configuration of a cell observation device 1 according to an embodiment of the present invention will be described with reference to FIG. 1. FIG. 1 is a schematic view showing the overall configuration of the cell observation device 1. As shown in FIG. 1, the cell observation device 1 is composed of an image acquisition unit 10 and a processing unit 20.

The image acquisition unit 10 is provided with a vessel 102 housing cells 101 as a sample, a culture space 103 maintained in a culture environment for the cells 101, an objective lens 104, a quantitative phase measurement light source 105, an illumination stop unit 105A, a reflection interference measurement light source 106, a half mirror 107, a dichroic mirror 108, a total reflection mirror 109, a reflection interference detection camera 110 (corresponding to "reflection interference imaging means" in the scope of claims), a diffractive interference optical system 111, and a quantitative phase detection camera 112 (corresponding to "quantitative phase imaging means" in the scope of claims). The half mirror 107 is an optical system for reflection interference incidence that is provided for guiding light from the reflection interference measurement light source 106 to the cells 101, and the dichroic mirror 108 is an optical system for reflection interference measurement that is provided for guiding light from the cells 101 to the reflection interference detection camera 110. The objective lens 104, the half mirror 107, and the dichroic mirror 108 constitute a common optical system for guiding light from an identical zone of the cells 101 to the reflection interference detection camera 110 and to the quantitative phase detection camera 112. Namely, in the present embodiment the reflection interference incidence optical system and the reflection interference measurement optical system are constructed as the common optical system. Furthermore, the total reflection mirror 109 and the diffractive interference optical system 111 constitute a quantitative phase optical system for guiding light to the quantitative phase detection camera 112. The reflection interference detection camera 110 images the light emitted from the reflection interference measurement light source 106 and reflected by the cells 101, to generate a reflection interference image (which corresponds to "reflection interference imaging step" in the scope of claims). The quantitative phase detection camera 112 images the light transmitted by the cells 101, of the illumination light emitted from the quantitative phase measurement light source 105 and passed through the illumination stop unit 105A such as a pinhole or an aperture, so as to turn into illumination light close to a point light source, thereby to generate a quantitative phase image (which corresponds to "quantitative phase imaging step" in the scope of claims). The quantitative phase measurement light source 105 to be used can be a light source with radiation sensitivity over a wide wavelength band such as a halogen lamp or a xenon lamp. The light source to be used may be one such as an LED (light emitting diode), a semiconductor laser (laser diode), or an SLD (super luminescent diode). In the case of the laser or the SLD, the illumination stop unit 105A can be omitted because the light source has a sufficiently small size.

The processing unit 20 is provided with a first processing unit consisting of an image alignment unit 201 (corresponding to "image alignment means" in the scope of claims), a first extraction unit 204 (corresponding to "first extraction means" in the scope of claims), and a second extraction unit 205 (corresponding to "second extraction means" in the scope of claims), a second processing unit consisting of a contour extraction unit 202 (corresponding to "contour extraction means" in the scope of claims), a contour application unit 203 (corresponding to "contour application means" in the scope of claims), and a third extraction unit 206 (corresponding to "third extraction means" in the scope of claims), and a third processing unit consisting of an analysis unit 207 (corresponding to "analysis means" in the scope of claims) and a reference storage unit 208 (corresponding to "reference storage means" in the scope of claims). The first processing unit, the second processing unit, and the third processing unit may be constructed as respective separate arithmetic devices or as a single arithmetic device.

The image alignment unit 201 is a unit that matches the spatial position of the reflection interference image with that of the quantitative phase image, thereby to implement alignment between the two images (corresponding to "image alignment step" in the scope of claims). The contour extraction unit 202 is a unit that extracts contours as zones of the cells 101, based on the quantitative phase image (corresponding to "contour extraction step" in the scope of claims). The contour application unit 203 is a unit that applies the contours extracted by the contour extraction means, to the reflection interference image, to generate a reflection interference image after contour application (corresponding to "contour application step" in the scope of claims).

The first extraction unit 204 is a unit that extracts a first parameter from the reflection interference image in alignment with the quantitative phase image by the image alignment means (corresponding to "first extraction step" in the scope of claims). The first parameter is information based on an adhesion state between the cells 101 and a substrate on which the cells 101 are laid. The information based on the adhesion state of the cells 101 to the substrate can be, for example, information such as an adhesion area of the cells 101 to the substrate, a ratio of the adhesion area to an overall imaging range, or an adhesion condition (pattern or two-dimensional distribution) of the cells to the substrate.

The second extraction unit 205 is a unit that extracts a second parameter from the quantitative phase image in alignment with the reflection interference image by the image alignment means (corresponding to "second extraction step" in the scope of claims). The second parameter is information based on (or indicative of) an optical thickness, an area, and/or a volume of cells 101, or a change in refractive index in the cells 101.

The third extraction unit 206 is a unit that extracts a third parameter from the reflection interference image after contour application (corresponding to "third extraction step" in the scope of claims). The third parameter is information based on an adhesion state to the substrate, in the contours of the cells 101. The information based on the adhesion state to the substrate in the range of the space occupied by the cells 101 can be, for example, information such as a ratio of the adhesion area to the overall area of the cells 101.

The reference storage unit 208 is a unit that preliminarily stores as reference data, parameters (the aforementioned first, second, and third parameters) extracted for cells of known types or states. The analysis unit 207 is a unit that determines a type or a state of a cell as an unknown specimen, based on the first, second, and third parameters extracted by the first extraction unit 204, the second extraction unit 205, and the third extraction unit 206. Specifically, the analysis unit selects a predetermined parameter from the first, second, and third parameters and determines a type or a state of a cell as an unknown specimen, using the predetermined parameter thus selected. The predetermined parameter may be a parameter indicative of a peculiar value automatically selected by the analysis unit 207 (or another processing means not shown), or a parameter selected by a user. The analysis unit 207 determines the type or the state of the cell as the unknown specimen, using the predetermined parameter thus selected. The analysis unit 207 may be configured to select the predetermined parameter, based on the reference data stored in the reference storage unit 208, and to determine the type or state of the cell as the unknown specimen, using it. Furthermore, when each of the first extraction unit 204, the second extraction unit 205, and the third extraction unit 206, or a combination thereof extracts three or more parameters, the analysis unit 207 may perform a principal component analysis on the three or more parameters to determine the type or state of the unknown cell. In the description hereinafter, a mode in which the analysis unit 207 selects the predetermined parameter based on the reference data and determines the type or state of the cell as the unknown specimen will be described in the section of [First Example]. On the other hand, a mode wherein the analysis unit 207 selects the predetermined parameter in accordance with a peculiar value or a user command, without basis on the reference data, and determines the type or state of the cell as the unknown specimen will be described in the section of [Fifteenth Example]. Furthermore, a mode wherein the analysis unit 207 determines the type or state of the unknown cell by the principal component analysis will be described in the section of [Sixteenth Example].

Figure 2:
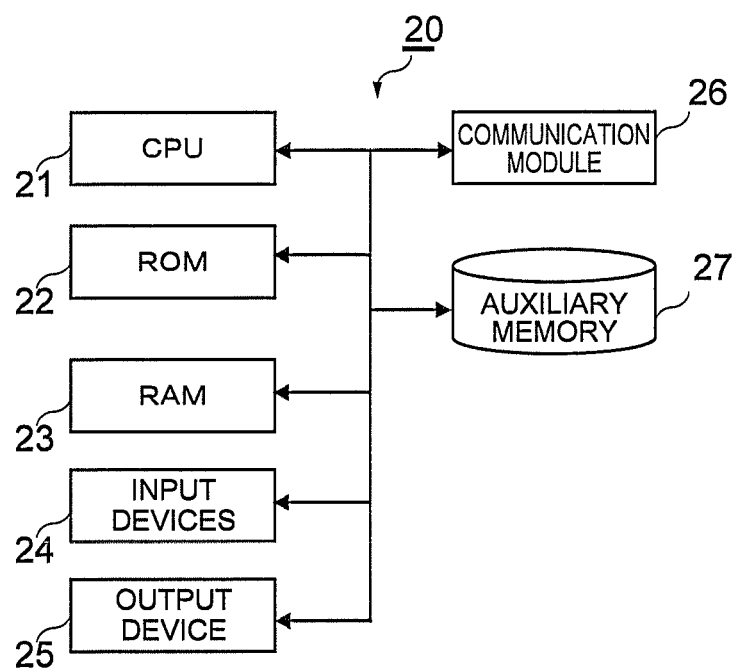
FIG. 2 is a hardware configuration diagram of a processing unit 20.

FIG. 2 is a hardware configuration diagram of the processing unit 20 having the functional constituent elements as described above. As shown in FIG. 2, the processing unit 20 is constructed, physically, as an ordinary computer system including a CPU 21, main memories such as ROM 22 and RAM 23, input devices 24 such as a keyboard and a mouse, an output device 25 such as a display, a communication module 26 such as a network card for transmission and reception of data to and from the image acquisition unit 10, and an auxiliary memory 27 such as a hard disk. Each of the functions of the processing unit 20 is substantialized in such a manner that predetermined computer software is retrieved onto the hardware such as the CPU 21, ROM 22, and RAM 23 to make the input devices 24, output device 25, and communication module 26 operate under control of the CPU 21 and data is read out and written into the main memories 22, 23 and the auxiliary memory 27.

[First Example]

The first example of the present invention will be described below in detail referring again to FIG. 1. FIG. 1 is the schematic configuration diagram of the cell observation device 1 according to the first example.

(Description of Image Acquisition Unit 10)

As shown in FIG. 1, the vessel 102 with the cells 101 as a measurement target therein is stationarily placed in the culture space 103 maintained in the culture environment for cells 101. The culture environment is an environment at controlled temperature, humidity, carbon dioxide concentration, etc. suitable for development or state maintenance of the cells 101.

The quantitative phase measurement will be described. The illumination light emitted from the quantitative phase measurement light source 105 disposed above the vessel 102 with the cells 101 therein, travels through the vessel 102 with the cells 101 therein, to be condensed by the objective lens 104. Then the light travels via the half mirror 107, then passes through the dichroic mirror 108 for separation of the quantitative phase image and the reflection interference image by wavelengths, and further travels via the total reflection mirror 109 to form an interference image between object light and reference light in the diffractive interference optical system 111 for phase measurement, and the interference fringe image is taken by the quantitative phase detection camera 112.

The reflection interference measurement will be described. The illumination light emitted from the reflection interference measurement light source 106 is reflected by the half mirror 107, and then travels through the objective lens 104 to enter the vessel 102 with the cells 101 as a measurement target therein, from the bottom side thereof. Without having to be limited to the half mirror 107, a beam splitter with a reduced reflection ratio, e.g., 5:95 (reflection:transmission) or 20:80 (reflection:transmission), may also be used if the intensity of the illumination light is sufficiently high. It is also possible to use a dichroic mirror with the reflectance and transmittance differing depending upon wavelengths. Reflected light from adhesion faces of the cells 101 on the bottom of the vessel 102 causes interference according to adhesion distances of the cells 101, and resultant reflection interference light is condensed again by the objective lens 104 and travels via the half mirror 107; only the reflection interference image is reflected by the dichroic mirror 108 for separation of the quantitative phase image and the reflection interference image by wavelengths, and picked up by the reflection interference detection camera 110. When a beam splitter such as a half mirror is used instead of the dichroic mirror 108, a filter for selection of the wavelengths to be used in reflection interference detection is to be placed between the beam splitter and the reflection interference detection camera 110. The light reflected from the adhesion faces of the cells 101 on the bottom of the vessel 102 has different amplitudes of interfering light depending upon the adhesion distances of the cells 101 and is imaged as a contrast of bright and dark patterns. Since the quantitative phase image and the reflection interference image are acquired through the common objective lens 104, the imaging range of the cells 101 is approximately the same in the quantitative phase measurement and the reflection interference measurement.

The camera 112 to acquire the quantitative phase image and the camera 110 to acquire the reflection interference image do not have to be limited to cameras of the same performance and same pixel resolution. Since quantities and wavelengths of the light beams incident into the respective cameras are different from each other, they may be cameras of performances and spatial resolutions suitable for the respective operations. For example, the quantitative phase detection camera 112 may be a sensitivity-priority camera with high sensitivity to 830 nm and with a large pixel size, and the reflection interference detection camera 110 may be a spatial-resolution-priority camera with high sensitivity to the visible range and with a small pixel size. This configuration requires a process of matching spatial coordinates of the two cameras, and this process will be described later.

In order to allow discrimination between the quantitative phase measurement and the reflection interference measurement by wavelengths, beams in different wavelength bands may be used for the respective illumination wavelengths of the reflection interference measurement light source 106 and the quantitative phase measurement light source 105. The dichroic mirror 108 can separate and select the quantitative phase image and the reflection interference image by the specific wavelengths. Accordingly, it becomes feasible to obtain the images at the same time without crosstalk by the quantitative phase measurement and the reflection interference measurement.

For observing as many cells 101 as possible, the device may be provided with a mechanism for moving the observation position. In order to minimize influence on the cells 101 and suppress vibration of the liquid level in the quantitative phase measurement, it is desirable to adopt a method of changing the observation position by moving the main body of the image acquisition unit 10 as an integrated body of the illumination optical system and the observation optical system on the XY plane, while keeping the vessel with the cells 101 therein stationary. At the same time, it is desirable to record plane coordinates in the XY space under observation on the images.

(Description of Processing Unit 20)

Figure 3:
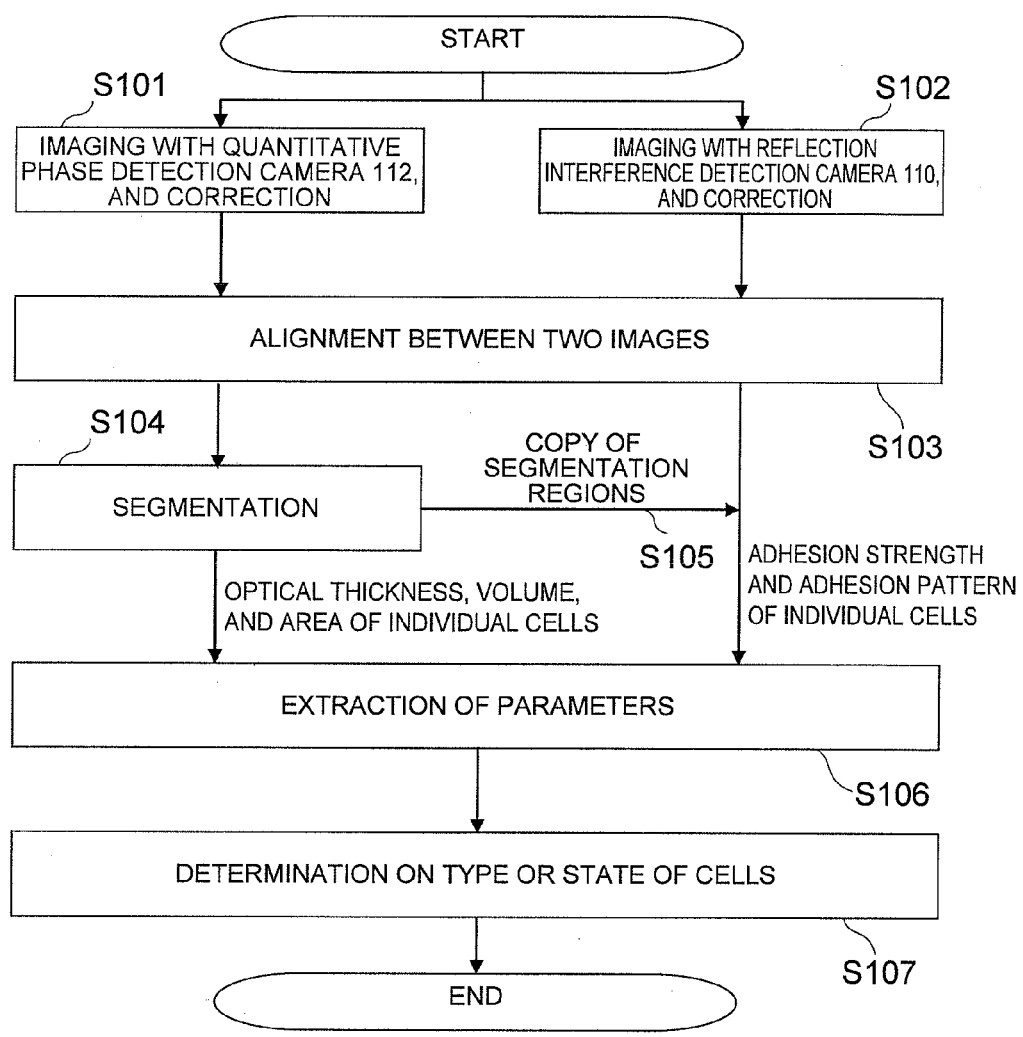
FIG. 3 is a flowchart showing functions and operation of the processing unit 20.

The functions and operation of the processing unit 20 will be described further referring to the flowchart of FIG. 3.

First, the quantitative phase detection camera 112 acquires the interference fringe image between reference light and, object light having passed through the cells 101 (step S101, corresponding to "quantitative phase imaging step" in the scope of claims). A quantitative phase image is formed from the interference fringe image by a well-known arithmetic method. For obtaining the quantitative phase image, an offset correction of the background region without the cells 101 and a shading correction in the field of the background region are carried out to make the background part spatially uniform and correct the phase value of the background part to 0, thereby obtaining a two-dimensional map of phases (optical path lengths) of the cells 101.

On the other hand, in parallel with the step S101, the reflection interference detection camera 110 acquires the reflection interference image of adhesion faces of the cells 101 (step S102, corresponding to "reflection interference imaging step" in the scope of claims). Since amplitudes of interference light are different depending upon distances of the cells 101 adhering to the bottom surface of the vessel 102, from the bottom surface of the vessel 102, the reflection interference image is taken as a contrast of bright and dark patterns. Correction is made for shading of reflected light in the field of the reflection interference image. At the same time an offset correction for the background part is carried out in each time unit, in order to prevent values of the background without the cells 101 from varying with time. Through these image arithmetic corrections, we can obtain the quantitative phase image and the reflection interference image with little spatial and temporal variations.

Figure 4:
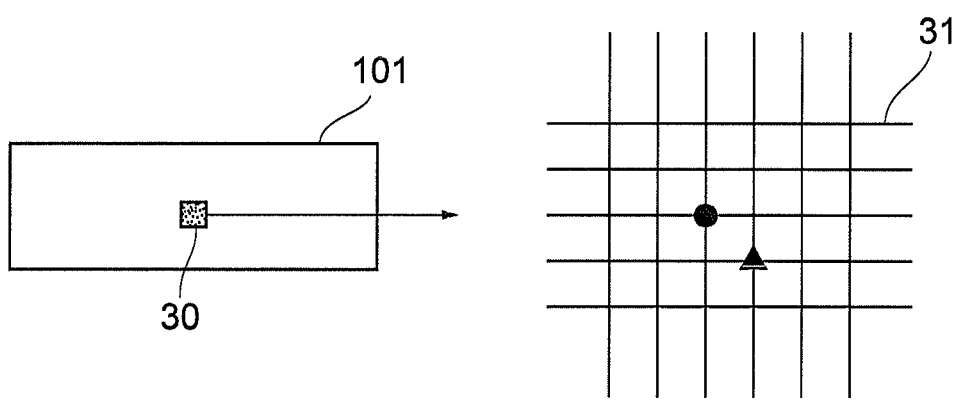
FIG. 4 is a drawing showing a sample 30 used in image alignment.

The next step is to perform a correction for spatial positions of the quantitative phase image and the reflection interference image (step S103, corresponding to "image alignment step" in the scope of claims). FIG. 4 shows a sample 30 used in image alignment. The sample 30 for alignment to be used herein can be a micro scale in which a grid 31 is scribed on a glass substrate, or a dot pattern. When the micro scale or the dot pattern is provided with at least one mark to identify the same position on images taken by the two cameras, the operation becomes simpler. In the example of FIG. 4, there are two marks, a triangle and a dot.

A procedure for shifting the image of the reflection-interference-side camera 110 so as to be aligned in position with the quantitative phase image will be described below in detail. First, the micro scale or the dot pattern is placed instead of the sample of cells 101 and is taken by each of the taking cameras for the reflection interference and the quantitative phase. Next, a reflection interference image and a quantitative phase image obtained by the photography of the micro scale or the dot pattern are superimposed on each other in respective different false colors (e.g., green for the reflection interference image and red for the quantitative phase image). In some cases the images become easily viewable with inversion of luminance thereof. Next, in order to match the grid image or dot image of the reflection interference image with the grid image or dot image of the quantitative phase image, while viewing the superimposed images, the reflection interference image is finely adjusted in (1) enlargement/reduction ratio, (2) horizontal movement amount (number of pixels), (3) vertical movement amount (number of pixels), (4) angle of rotation, (5) direction of rotation, (6) mirror reversal, etc. to determine adjustment amounts thereof. The adjustment amounts can be determined to achieve such position that the grid images or dot images displayed in superposition overlap each other with no edges projecting out, for example, such position that the grid images or dot images overlap each other to turn green and red into yellow.

If the two camera images taken have spatial distortions and patterns of the spatial distortions of the two images are largely different, it is sometimes difficult to equally match the positions of all the pixels by the aforementioned data (1) to (6) only. In such cases movement amounts are different for all the pixels in the field and it is thus necessary to determine the movement amounts for the respective pixels. Specifically, shift amounts of respective points are determined so as to match intersections of the grid images or center coordinates of respective dots of the dot images with each other between the two cameras. Shift amounts for spatial coordinates except for the coordinates where the grid or dots exist are determined by interpolation. A table is created by storing the shift amounts in pixel unit for spatially all pixels (all coordinates) in this manner, and is defined as alignment data. The alignment data thus obtained is stored as a file. When new measurement is performed to acquire images, alignment between the images is carried out using the alignment data stored in the file, and position-corrected images are output. When the image data acquired through execution of new measurement is stored in a file, the alignment data is preferably stored together with the image data in the file. This allows the device to quote the alignment data, which was the best in new acquisition of the images, in calling of the image file and to correct the called images.

The alignment as described above does not have to be performed every measurement of quantitative phase and reflection interference, but may be performed, for example, at the frequency of once per month, with consideration to positional deviation due to influence of the use environment and vibration, as long as the same optical system is used. If the observation-side optical system is equipped with a component to select a filter for observation (e.g., an electric filter wheel), the alignment is preferably performed for each filter to be used. The reason for it is that positional deviation amounts and directions of positional deviation of images differ depending upon inclination or parallelism of the filter to be used.

Although description is omitted to avoid redundancy, the above procedure can also be suitably applied to the case opposite to the above, i.e., the case where the image of the quantitative-phase-side camera 112 is shifted in position so as to match the reflection interference image. The above procedure can be carried out without the aid of human hand by automated image processing.

Referring back to FIG. 3, after the alignment in the step S103, a process of extracting contour regions of the cells 101 (which will also be referred to hereinafter as "segmentation") is carried out (steps S104 and S105, corresponding to "contour extraction step" and "contour application means" in the scope of claims).

Figure 5:
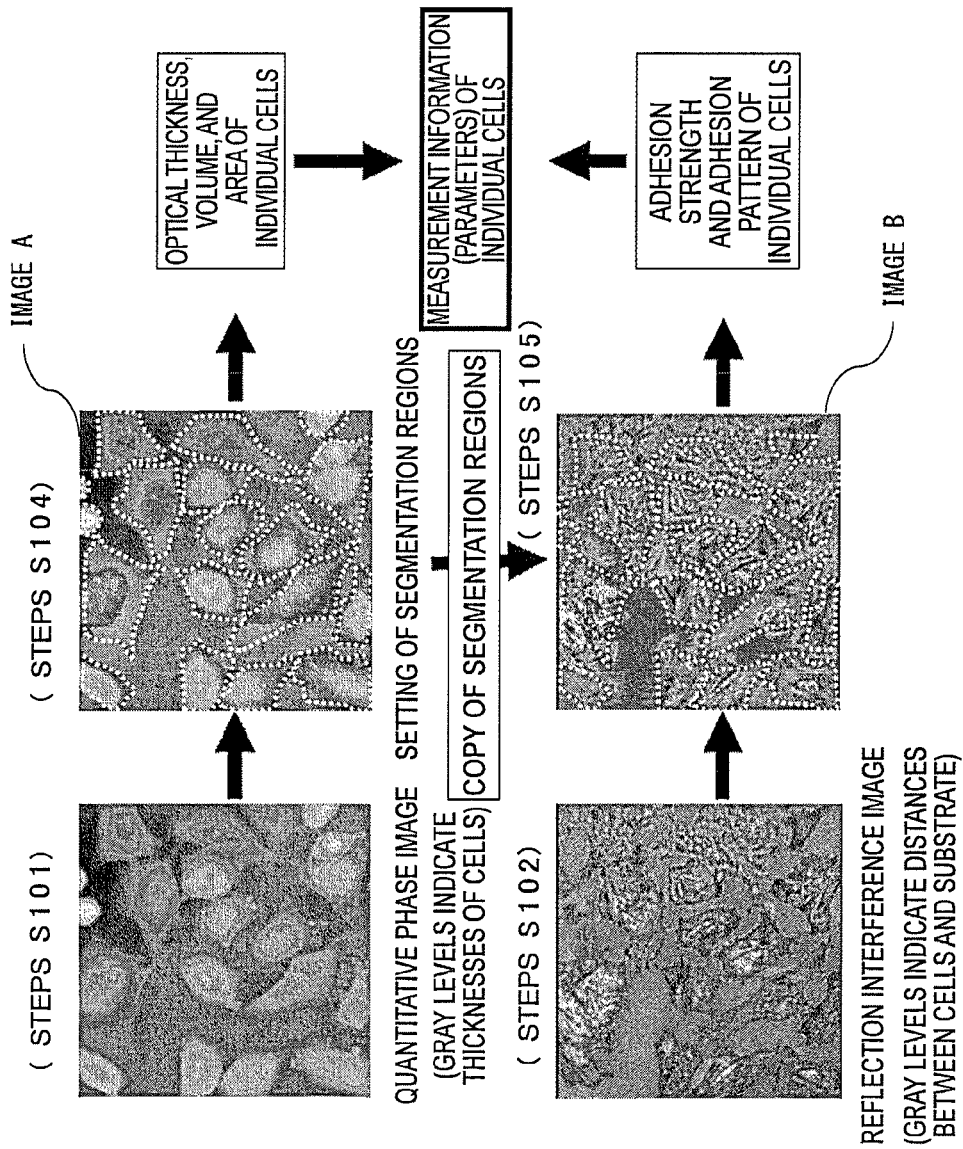
FIG. 5 is a drawing showing an example of a contour extraction process and a contour application process.

First, as shown in FIG. 5, regions as contours of individual cells 101 are detected from the quantitative phase image out of the quantitative phase image and the reflection interference image after taken at the same time and aligned with each other, by image processing (step S104, image A in FIG. 5, corresponding to "contour extraction step" in the scope of claims). Namely, in the quantitative phase image, the optical path lengths of light passing through the cells 101 become longer than those of light passing through the solution as the background without the cells 101 therein, because the refractive index of the cells 101 is larger than that of the solution. For this reason, phase values of pixels in the regions where the cells 101 exist become larger than those in the background. Therefore, when an appropriate threshold or spatial filtering process is applied, the cells 101 can be separated from the background automatically without the aid of human hand. Then the contours corresponding to the respective cells 101 can be determined and regions of pixel coordinates corresponding to the regions occupied by the respective cells 101 can be determined.

Next, the pixel coordinates of the contour regions of the individual cells 101 obtained in step S104 are adapted to the reflection interference image aligned in spatial coordinates, i.e., the segmentation regions obtained in step S104 are copied onto the reflection interference image, whereby the contour regions of the individual cells 101 determined on the quantitative phase image are applied to the reflection interference image (step S105, image B in FIG. 5, corresponding to "contour application step" in the scope of claims). By this step, as shown in FIG. 5, the same contour regions can be determined for the two images A, B of the quantitative phase image and the reflection interference image.

After the segmentation in steps S104 and S105, a process of extracting parameters is then carried out (step S106, corresponding to "first extraction step," "second extraction step," and "third extraction step" in the scope of claims).

Namely, in the regions of the respective cells 101 obtained in step S104, the second extraction unit 205 acquires from the quantitative phase image, (1) an average value of optical thicknesses (optical path lengths) of the cells 101, (2) a standard deviation of optical thicknesses, (3) an area of the cells 101, and (4) an optical volume of the cells 101 (a total value of optical thicknesses) (step S106, corresponding to "second extraction step" in the scope of claims). Furthermore, from the reflection interference image aligned in step S103 and the reflection interference image with the copy of the segmentation regions obtained in step S105, the first extraction unit 204 and the third extraction unit 206 each obtain (5) an average luminance of bright and dark regions, (6) an area of dark regions indicating strong adhesion, (7) an area of bright regions indicating weak adhesion, (8) ratios of dark regions to the overall imaging range and to the area of cells 101, and (9) ratios of bright regions to the overall imaging range and to the area of cells 101 (step S106, corresponding to "first extraction step" and "third extraction step" in the scope of claims).

A quantitative analysis to analyze a texture obtained from the two-dimensional intensity distribution pattern of bright and dark regions of the reflection interference image is carried out as a method to obtain a two-dimensional distribution pattern of adhesion portions. The texture analysis is performed by applying the co-occurrence matrix method to acquire features of the texture obtained from a co-occurrence matrix with elements of probabilities $P(i,j)$ ($i,j=0, 1, 2, 3, \ldots n-1$) that a gray level of a pixel distant by the distance of d pixels in the $\theta$-direction from a pixel with a gray level i in the image is j, the gray level histogram method to acquire features of the texture from a gray level histogram P(i) in the image, and so on. This analysis process may be carried out by the analysis unit 207.

Examples of feature parameters of the texture obtained by the co-occurrence matrix method include (10) energy, (11) entropy, (12) correlation, (13) local uniformity, (14) inertia, and so on. Among these, energy is an index indicating whether the probability distribution of the co-occurrence matrix is concentrated at a specific value, and entropy an index indicating whether the probability distribution of the co-occurrence matrix is distributed over values in a wide range. On the other hand, examples of feature parameters of the texture obtained from the gray level histogram method include (15) average, (16) variance, (17) skewness, (18) kurtosis, and so on. Among these, skewness is an index indicating how far the shape of the gray level histogram deviates from a symmetric shape, and kurtosis an index indicating how close the distribution of the gray level histogram is concentrated around an average.

Since the parameters of (12) correlation by the co-occurrence matrix method and (15) average and (16) variance by the gray level histogram method among those are readily affected by brightness of luminosity upon acquisition of the image, evaluation had better be made by capturing a condition that they are limited to those acquired in the same exposure duration and at the same illumination luminance, for example. In this case, (19) "$\sqrt{}$ (variance)/average luminosity" can be used instead of variance, whereby it can be used as a parameter that is not affected by the condition of brightness upon acquisition of the image. In the co-occurrence matrix method, we can obtain a plurality of values about the direction θ and distance d, and a large number of parameters can be optimized if a preliminary experiment is carried out in advance to investigate and determine differences of parameters among cells with any direction and any distance. The result this time will be obtained by fixing the θ-direction=0° and the distance d=8 pixels. Numerical values of the parameters (1) to (19) about the individual cells 101 obtained in this manner are stored as the measurement result.

Figure 7:
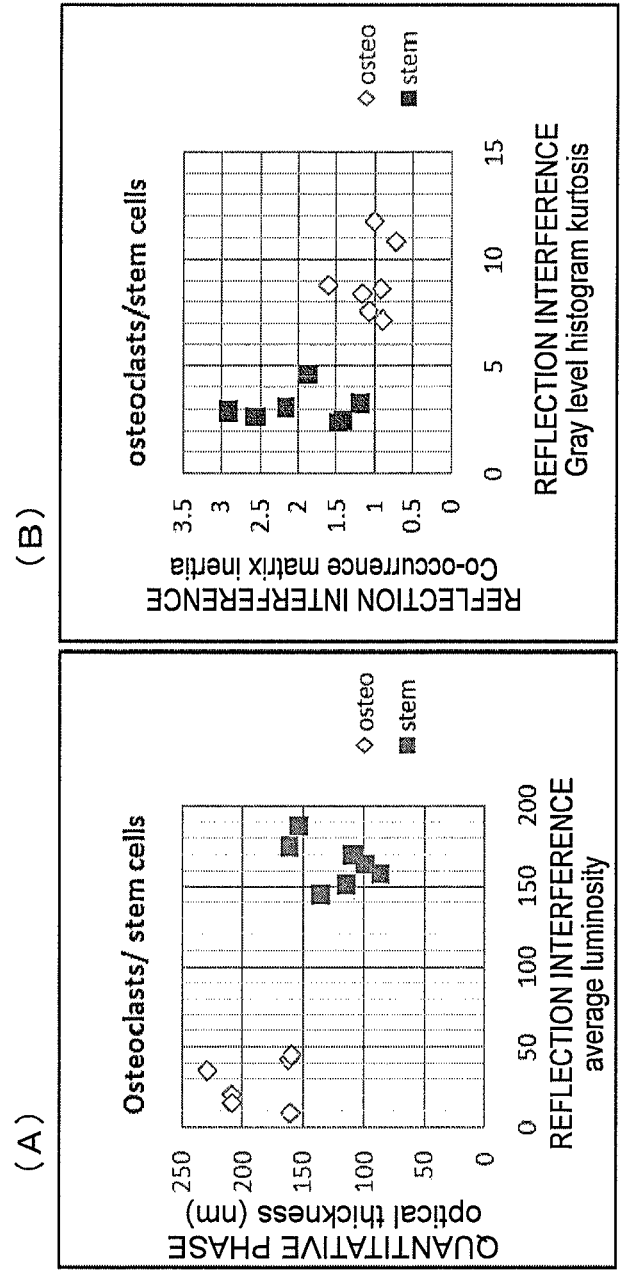
FIG. 7 is an example of two-component scatter diagrams created using extracted parameters.

FIG. 6 shows an example of the parameters obtained from the individual cells. A scatter diagram can be drawn using two components out of these parameters. FIG. 7 is plots using characteristic parameters for discrimination as to two types of cells, myeloid stem cells and differentiation-induced osteoclasts. (A) in FIG. 7 is a two-component scatter diagram as a plot of the respective types of cells in which the horizontal axis represents the average luminosity (5) of bright and dark patterns in reflection interference and the vertical axis the average (1) of optical thicknesses of cells in quantitative phase. On the other hand, (B) in FIG. 7 is a plot in which the horizontal axis represents the kurtosis (18) in the gray level histogram method of the texture analysis in reflection interference and the vertical axis the inertia (14) in the co-occurrence matrix method of the texture analysis in reflection interference. In either of the two-component scatter diagrams, stem cells and osteoclasts form their respective groups and thus the parameters are effective to discrimination of different types of cells.

Referring back to FIG. 3, based on the measurement information (parameters) obtained from the individual cells 101 in step S106, it is determined to which type of cell group the cells as the unknown specimen are similar, or to which state of cell group the cells as the unknown specimen are similar (step S107). For this determination, measurement information on known states of cell groups is preliminarily stored as reference data and the type or state of the cells as the specimen is determined by comparing the specimen cells with the reference data. The cell observation device 1 is provided with the reference storage unit 208 for storage of the reference data, as shown in FIG. 1. The reference storage unit 208 can store a plurality of types of cells or a plurality of types of states of cells, can also have a reference about a typical cell group as a default value, and can also store additional data obtained through execution of new measurement with a cell group necessary for an operator.

A procedure of acquiring the reference data includes first preparing multiple cells from a known type of cell group or a known state of cell group in advance. These cells to be prepared should be cells with little variation among them and with quality as homogenous as possible. Next, the aforementioned processes of steps S101 to S106 are carried out for these cells by collaboration of the image acquisition unit 10 and the processing unit 20 and the measurement result obtained is stored as reference data in the reference storage unit 208.

Figure 8:
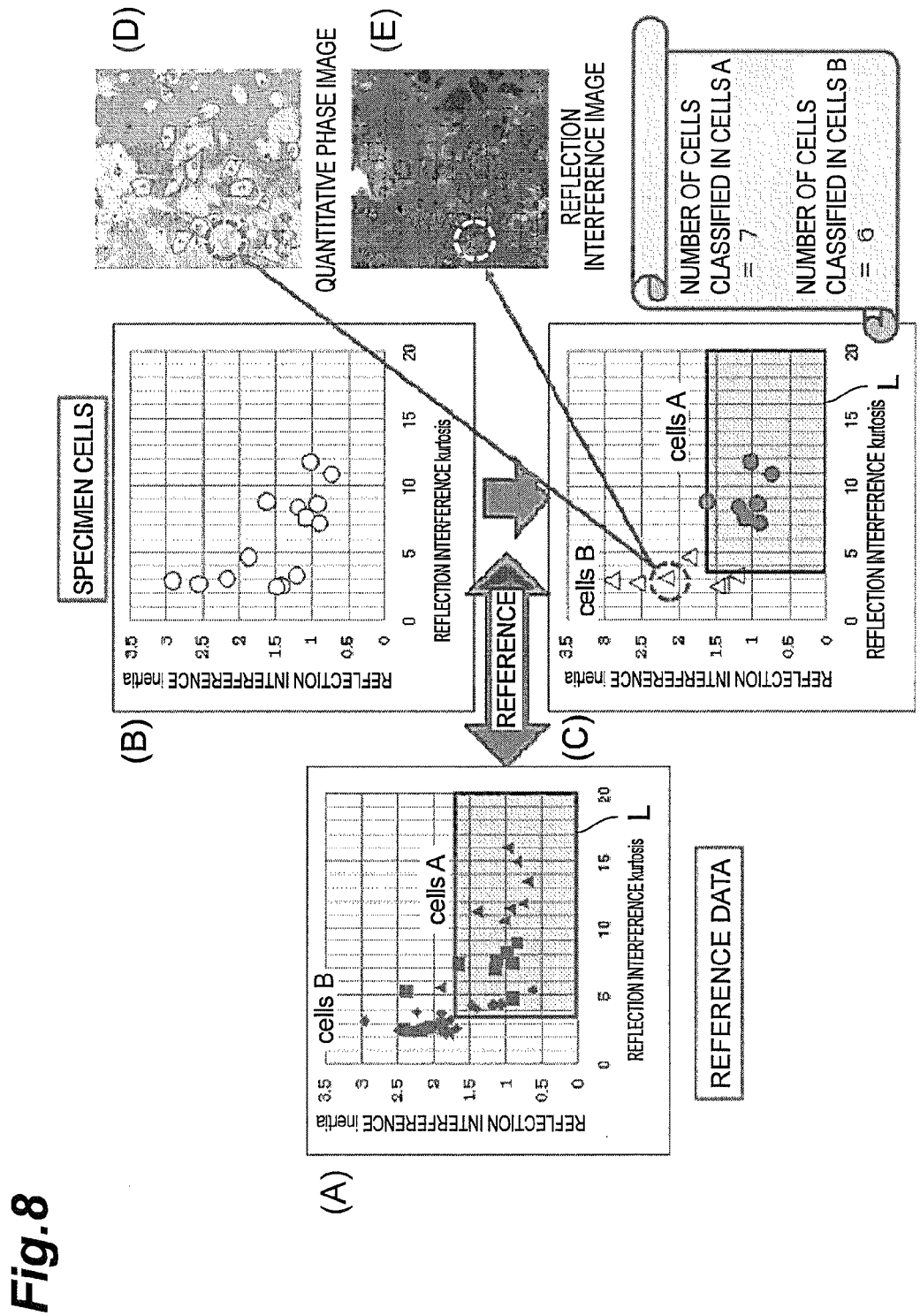
FIG. 8 is a drawing showing an example in which cell determination was conducted using reference data.

Let us consider a situation in which it is determined to which unknown cells as a specimen belong between two cell groups, as an example of cell determination using the reference data. The following determination process is carried out by the analysis unit 207. First, as to two types of cell groups stored as reference, arbitrary two components are selected from the measurement result of (1) to (19) of the individual cells and two-component scatter diagrams are created with the two components on the vertical axis and on the horizontal axis, respectively. Among the two-component scatter diagrams thus created, a two-component scatter diagram to allow simple discrimination between the two cell groups by a simple partition line is used as determination criteria in discrimination of cells as a specimen. For example, in the case of the reference data as an example shown in (A) of FIG. 8, a scatter diagram is obtained as means for discrimination between cells A and cells B by plotting the kurtosis (18) in the gray level histogram method of the texture analysis in reflection interference on the horizontal axis and plotting the inertia (14) in the co-occurrence matrix method of the texture analysis in reflection interference on the vertical axis. Use of this two-component scatter diagram allows discrimination between cells A and cells B by a simple partition line L. The discrimination can be made with the sensitivity of 100% and the specificity of 100%, as the performance of the discrimination of cells A with this partition line L.

Next, measurement is carried out for unknown cells as a specimen and parameters of the measurement result of (1) to (19) described above are obtained for each of unknown cells. When discrimination is to determine whether the cells as a specimen are cells A or cells B, the two-component scatter diagram of reference data for discrimination between cells A and cells B is called and reference is made thereto. As shown in (B) and (C) of FIG. 8, the specimen cells are plotted on the two-component scatter diagram of reference data and the regions corresponding to cells A and cells B are clearly shown using the partition line L. Then the specimen cells lie in the region of cells A or in the region of cells B partitioned by the partition line L, and it becomes feasible to determine to which cell group the specimen cells belong. In (C) of FIG. 8, the result obtained is such that seven cells out of the thirteen specimen cells are classified in cells A and remaining six cells in cells B. Of course, as shown in (D) and (E) of FIG. 8, it is also possible to clearly show each data value plotted on the two-component scatter diagram in association with any one of cells on the quantitative phase image and on the reflection interference image.

The partition line may be provided as a rectangular region parallel to the vertical and horizontal axes by visual inspection on the two-component scatter diagram, or a linear discriminant to distinguish two groups may be applied by use of the discriminant analysis technique of statistical analysis. When cells are discriminated by a linear discriminant, discriminant scores are obtained based on the linear discriminant obtained, for individual cells, and then one of two groups takes positive values of discriminant scores and the other negative values, thus permitting simple discrimination of cells.

(Operation and Effects of First Example)

The below will describe the operation and effects of the cell observation device 1 according to the first example described above. The cell observation device 1 of the present example is provided with the reflection interference measurement unit consisting of the reflection interference measurement light source 106, the reflection interference detection camera 110, and the first extraction unit 204, whereby the first parameter is obtained based on the reflected light from the cells. The device is also provided with the quantitative phase measurement unit consisting of the quantitative phase measurement light source 105, the quantitative phase detection camera 112, and the second extraction unit 205, whereby the second parameter is obtained based on the transmitted light from the cells. As described above, the cell observation device 1 of the present example is provided with both of the reflection interference measurement unit and the quantitative phase measurement unit so as to be able to acquire both of the first parameter and the second parameter, which allows the user to obtain the greater amount of information to appropriately determine and evaluate the state of cells. Furthermore, the first parameter is extracted from the reflection interference image in alignment with the quantitative phase image and the second parameter is extracted from the quantitative phase image in alignment with the reflection interference image; therefore, it can be said that there is consistency achieved between the two parameters as to any part of cells. Namely, the alignment between the two images by the image alignment unit 201 in the present example makes the two parameters applicable as parameters to determine and evaluate a state of an identical portion of cells.

In the present example, the third parameter is further obtained in addition to the first parameter and the second parameter. Since this third parameter is a parameter obtained after matching of cell contours between the quantitative phase image and the reflection interference image, it is different in property from the first parameter and the second parameter and when the user further obtains this third parameter, the user has a greater amount of information to appropriately determine and evaluate the state of cells.

There is no user's intervention in the process of generating the reflection interference image after contour application by extracting the contours of cells from the quantitative phase image and applying the contours to the reflection interference image. On the other hand, the conventional method with the reflection interference microscope (reflection interference method) requires preliminary recognition of contours of individual cells and therefore the reflection interference method is often used in combination with another method for contour recognition. As described above, Non Patent Literature 1 above discloses the combination of the reflection interference method with the fluorescence method, but the operator determines the contours of cells by handwriting because it was difficult to automatically extract the cell contours. Non Patent Literature 2 discloses the combination of the reflection interference method with the transmission illumination method but mentions nothing about automatic determination of cell contours without the aid of human hand. Furthermore, Non Patent Literature 3 discloses the combination of the reflection interference method with the bright field method and mentions automatic extraction of cell contours, more or less; however, for example, it describes that the user needs to manually set the optimum threshold for contour extraction while viewing the bright field image, and thus admits the necessity for user's intervention to some extent, thus failing to automatically determine the cell contours without the aid of human hand. In contrast to it, in the present example the processing including the cell contour extraction from the quantitative phase image, the application of the contours to the reflection interference image, and the generation of the reflection interference image after contour application is carried out in the unaided manner by the contour extraction unit 202 and the contour application unit 203. The unaided execution of these processes remarkably improves the work efficiency and achieves considerable reduction in operation time in conjunction therewith.

To determine how much the operation time can be reduced by automatization of the segmentation by the contour extraction unit 202 and the contour application unit 203, an experiment was conducted in comparison with the case of Non Patent Literature 3. Approximately a hundred cells existing in the field were photographed in the bright field (in the case of Non Patent Literature 3) and in the quantitative phase (in the case of the present example), and the time necessary for the segmentation process was measured for each of them. In the bright field case, it was difficult to perform the segmentation with a threshold of brightness, and therefore the segmentation was carried out by tracing each of contours of cells with a mouse by an operator's hand having ordinary work performance. In this case, 150 seconds were needed for the segmentation of a hundred cells. On the other hand, in the case of the phase image of cells obtained in quantitative phase, the segmentation was carried out by the automatic threshold and image processing in the contour extraction unit 202 and the contour application unit 203. In this case, a hundred and eight cells were segmented in an operation processing time of three seconds, thereby achieving the significant time reduction from 150 seconds to 3 seconds. As understood from the above experiment result, when the segmentation is carried out in the unaided manner with provision of the contour extraction unit 202 and the contour application unit 203 of the present example, the work efficiency improves remarkably and the significant reduction in operation time is achieved in conjunction therewith.

In the present example, the information based on the adhesion state of cells to the substrate is obtained including the information such as the adhesion area of cells to the substrate, the ratio of the adhesion area to the overall imaging range, and the adhesion condition (pattern and two-dimensional distribution) of cells to the substrate, and the user is allowed to appropriately determine and evaluate the state of cells, using these pieces of information.

In the present example, the information obtained includes the information based on the optical thickness, area, and volume of cells, or the change of refractive index in cells, and the user is allowed to appropriately determine and evaluate the state of cells, using these pieces of information.

In the present example, the information such as the ratio of the adhesion area to the overall area of cells is obtained as information based on the adhesion state to the substrate in the contours of the cells, i.e., in the range of the space occupied by the cells, and the user is allowed to appropriately determine and evaluate the state of cells, using this kind of information.

In the present example, the user is allowed to determine the type or state of cells as an unknown specimen, based on the reference data.

[Second Example]

The second example of the present invention will be described below. The second example includes all the constituent elements of the first example shown in FIG. 1 and is further characterized by the quantitative phase measurement light source 105.

Conventionally, the light source for acquisition of phase change frequently used was one to emit a laser light beam with high coherency. However, when the laser beam is used, the measurement is often affected by background noise due to excessive interference originating in an optical system such as an objective lens or by scattering light noise from high-index granules in cells. The quantitative phase measurement in the cell observation device 1 of the present example is characterized by using low-coherent light with a wide wavelength band and with low coherency, as the illumination light source. This feature can reduce the noise due to excessive interference and ensure stabler measurement. In an example, the noise due to excessive interference was reduced by use of an SLD (super luminescent diode) with the center wavelength of 830 nm and the wavelength band of about 20 nm, thus succeeding in stabler measurement.

[Third Example]

The third example of the present invention will be described below. The third example includes all the constituent elements of the first example shown in FIG. 1 and is further characterized by the reflection interference measurement light source 106.

Conventionally, the illumination light used for obtaining a sufficient contrast was illumination light with the use of a band-pass filter to limit the wavelength band to some extent. However, the band-passed illumination light has high coherency and it was often the case that interference fringes are reflected in the image due to reflection from interfaces between a culture solution and upper cell membranes of cells unrelated to the adhesion faces of cells. The reflection interference measurement in the cell observation device 1 of the present example uses low-coherent light with a wide wavelength band and with low coherency. The use of the illumination light with the wide wavelength band can narrow the distance of occurrence of interference and allows the reflection interference image to be taken as being limited to the adhesion faces of the cells to the substrate.

Figure 9:
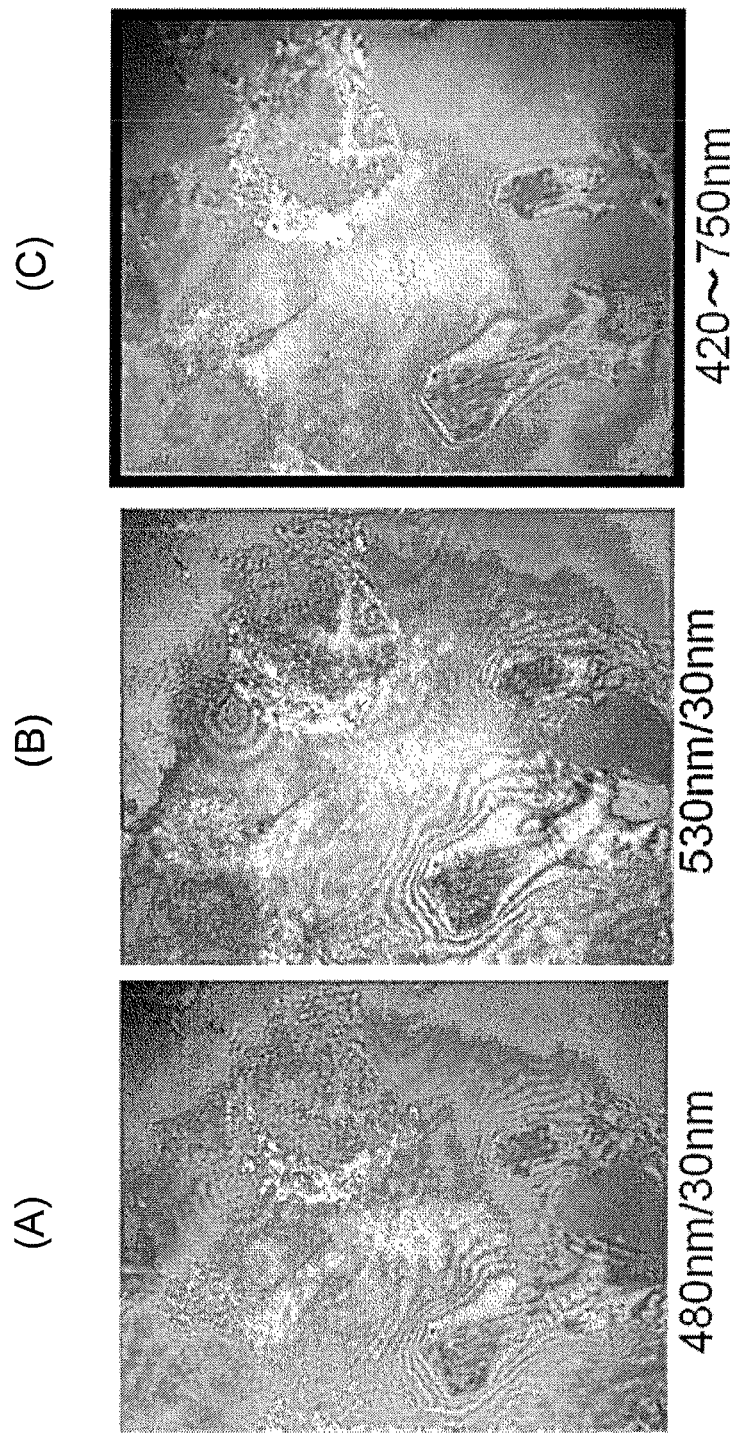
FIG. 9 is a drawing for showing an effect by a third example.

FIG. 9 shows the difference of the reflection interference image with the use of the illumination light having the wide wavelength band of 420 nm to 750 nm from those with the use of the illumination light band-passed in the narrow wavelength band of about 30 nm around the center wavelength of 480 nm or 530 nm. With the illumination light band-passed in the narrow wavelength band as shown in (A) of FIG. 9 and (B) of FIG. 9, reflection from interfaces between the culture solution and the upper cell membranes of cells different from the adhesion faces of cells is observed like interference fringes over the image, whereas with the use of the illumination light having the wide wavelength band as shown in (C) of FIG. 9, no interference is observed due to reflected light from the upper parts of cells and thus it becomes feasible to extract only the information more limited to the adhesion faces of cells.

In the present example, the light source used is a halogen lamp with a wide band of radiation wavelengths and output light therefrom is passed through a band-pass filter with an arbitrary wide wavelength band in the visible-to-near infrared wavelength zone from about 420 nm to about 800 nm. The reflection interference image can be extracted as being limited to the adhesion faces of cells, with the use of the band-passed light having the center wavelength of 500 nm to 1000 nm and the full width at half maximum of not less than 100 nm. Such devising of illumination is very effective in acquisition of quantitative parameters from cells.

[Fourth Example]

Figure 10:
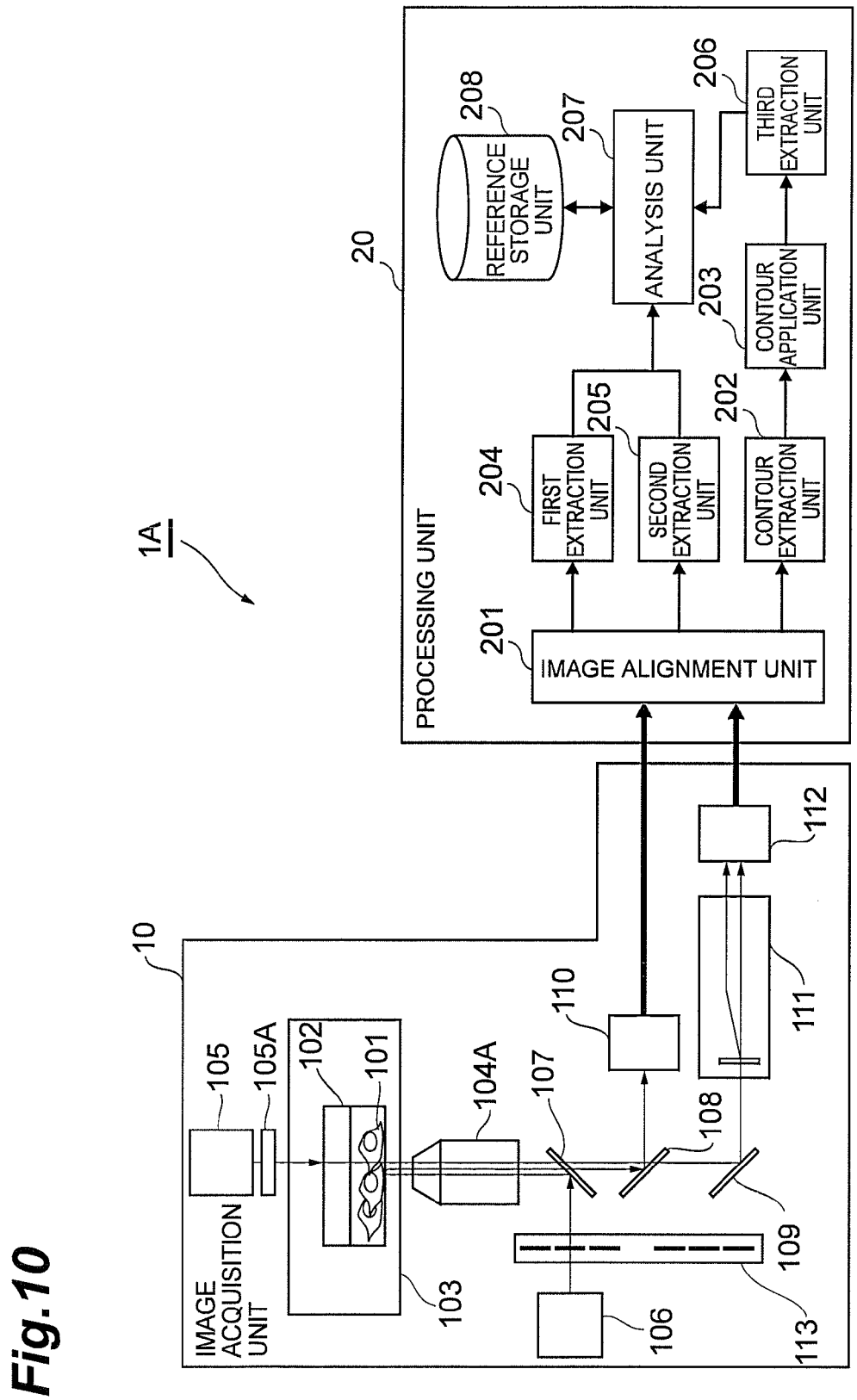
FIG. 10 is a schematic diagram of a configuration of a cell observation device 1A according to a fourth example.

The fourth example of the present invention will be described below. The fourth example includes all the constituent elements of the first example shown in FIG. 1 and is further characterized by the illumination method for acquisition of the reflection interference image. FIG. 10 is a schematic diagram of a configuration of a cell observation device 1A according to the fourth example. As shown in FIG. 10, the cell observation device 1A is further provided with a ring slit 113.

In general, measurement has to be carried out with as many cells as possible, in order to acquire statistically significant data or to discover dissimilar cells rarely mixed in a large number of cells. For that purpose, it is desirable to measure a wide field at once with the use of an objective lens having a magnification as low as possible. However, a low-magnification objective lens has a low NA, and illumination light with a low NA includes a lot of components impinging vertically on a sample and causes a phenomenon in which the light is reflected at the interface between air and a solution present above the cells and the cells are illuminated with reflected light. This causes a morphological image of cells unrelated to the adhesion faces, to be included on the observation side. Furthermore, the illumination light passing through the central region of the objective lens is reflected inside the objective lens, and the reflected light is included in a large quantity on the observation side to become high background light, causing reduction in contrast of the reflection interference image of adhesion faces.

In the reflection interference measurement in the cell observation device 1A according to the present example, when a low-NA objective lens 104A is used, as shown in FIG. 10, a slit 113 of a ring shape is disposed at a position conjugate with an aperture stop on the reflection interference measurement light source 106 side of the objective lens 104A. The illumination light from the reflection interference measurement light source 106 passes through the slit 113 opening in the ring shape and thus the illumination light passes through the periphery without passing through the center of the objective lens 104A; therefore, the cells 101 are illuminated with the use of only high-NA angled light, which can reduce the influence of reflected light from the solution above the cells 101. The illumination using the ring-shape slit 113 can reduce not only the reflection due to the low-NA objective lens 104A, but also generally the background light due to the reflection inside the objective lens 104A. For allowing the slit 113 opening in the ring shape to be changed for each objective lens 104A so as to adapt to the pupil diameter of the objective lens 104A to be used, a plurality of ring slits 113 adapting to respective objective lenses 104A to be used are mounted on a disk and the disk is rotated according to needs, thereby achieving a configuration to allow the user to select one of the ring slits 113.

FIG. 11 shows the reflection interference image without use of the ring slit 113 and the reflection interference image with use thereof. (A) in FIG. 11 shows the reflection interference image without use of the ring slit 113. The cells are illuminated with reflected light from the interface between the solution above the cells and air and a cell contour image is observed over the adhesion image of cells, as indicated by an arrow. On the other hand, in the case where the illumination optical system is provided with the ring slit 113, as shown in (B) of FIG. 11, illumination components traveling straight toward the interface between the solution above the cells and air are cut so as to prevent the cells from being illuminated with reflected light from the top, and therefore the information on the adhesion faces of cells can be observed with good contrast. Such devising of illumination is very effective in acquisition of quantitative parameters from the cells.

[Fifth Example]

The fifth example of the present invention will be described below. The fifth example includes all the constituent elements of the first example shown in FIG. 1 and is further characterized by the vessel housing the cells 101.

Figure 12:
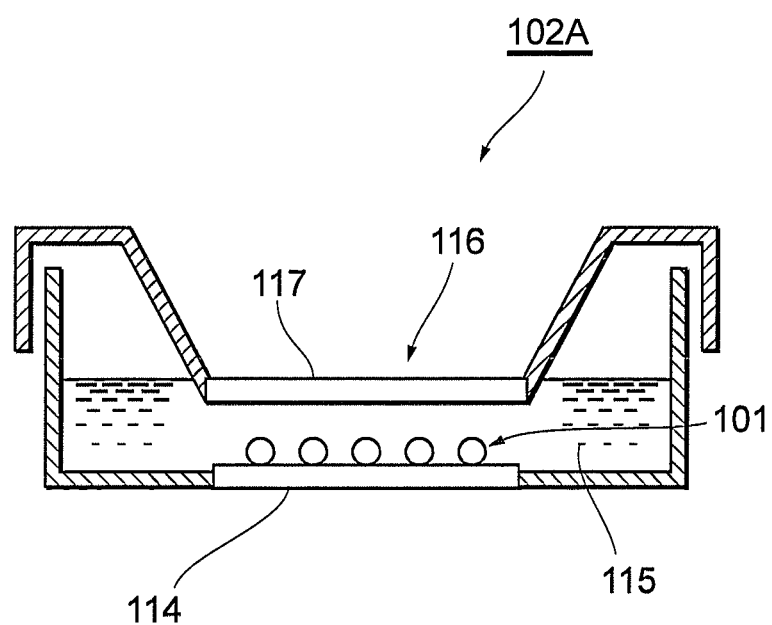
FIG. 12 is a drawing showing a vessel 102A in a fifth example.

FIG. 12 is a drawing showing the vessel 102A in the fifth example. One of features of the vessel 102A is an antireflection coat 114 on the side opposite to the adhesion faces of cells 101 in the vessel 102A housing the cells 101 (or on the objective lens side of the observation area of the vessel 102A) (which will also be referred to hereinafter as "feature 1"). One of the other features of the vessel 102A is provision of an observation window 116 such as glass parallel to such a height as to contact the culture solution 115, in order to keep the height of the culture solution 115 constant, in the upper part of the vessel 102A (which will also be referred to hereinafter as "feature 2"). Still another feature of the vessel 102A is an antireflection coat 117 on the observation window 116 outside the vessel 102A (or on the air side opposite to the face in contact with the culture solution 115) (which will also be referred to hereinafter as "feature 3").

Feature 1 exerts a pronounced effect on acquisition of the reflection interference image. For the purpose of measuring the cells 101 as many as possible, it is preferable to use a low-magnification objective lens. However, the low-magnification objective lens has a low NA, which is usually not of an oil immersion or water immersion type, but is generally an objective lens of a dry type. However, when the reflection interference image is taken using the objective lens of the dry type, the illumination light emerging from the objective lens is significantly reflected on the bottom surface of the vessel housing the cells 101. This is because the refractive index difference between air and glass of the bottom surface of the vessel is large. For this reason, the background light increases considerably and it becomes almost difficult to observe the reflection interference image of the adhesion faces of cells 101. This is the reason why the objective lens of the oil immersion or water immersion type has been used heretofore for reflection interference observation.

Figure 13:
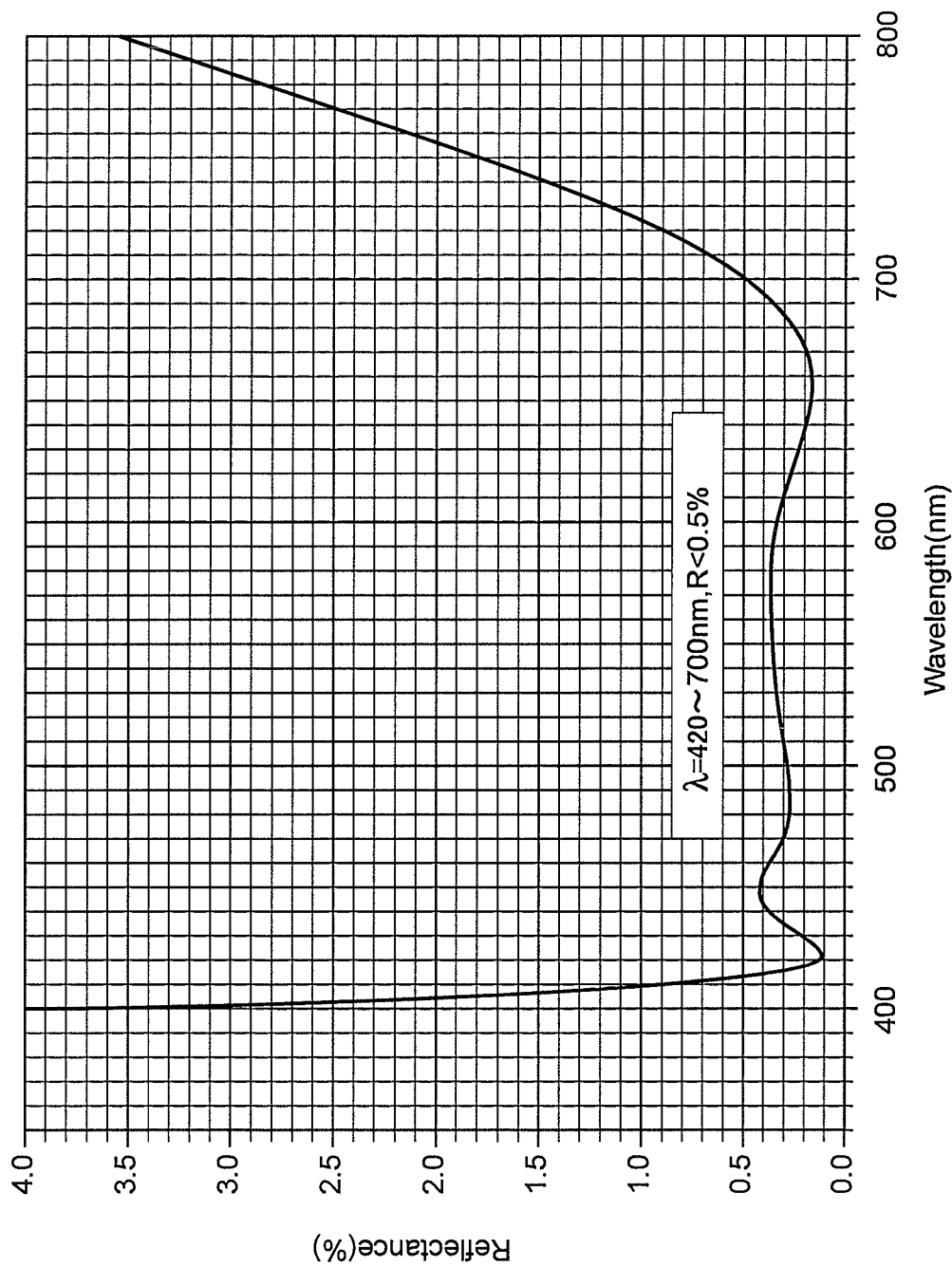
FIG. 13 is a drawing for showing an effect by the fifth example.

Therefore, the fifth example enabled the acquisition of the reflection interference image with the use of the objective lens of the dry type, by providing the antireflection coat 114 on the side opposite to the adhesion faces of the cells 101 in the vessel 102A housing the cells 101 (or on the objective lens side of the observation region of the vessel 102A). As shown in FIG. 13, the illumination light from the objective lens without the antireflection coat 114 is reflected approximately 4% at the interface between air and glass, whereas when the bottom surface of glass is subjected to an antireflection coat treatment to control the reflectance R to about 0.5% in the wavelength range of the illumination light (420 nm to 720 nm), the background light can be reduced to one eighth or below. For this reason, the fifth example allows the reflection interference image of the cell adhesion faces to be obtained with high contrast, even with the use of the objective lens of the dry type.

FIG. 14 shows the reflection interference image taken with the use of the dry objective lens in the configuration where the antireflection coat 114 is laid on the bottom surface of the vessel 102A. Without the antireflection coat 114, as shown in (A) of FIG. 14, the reflection interference image comes to have extremely low contrast because of the significant reflection from the bottom surface of the vessel 102A. In contrast to it, when the vessel used is the vessel 102A with the antireflection coat 114 on the bottom surface, as shown in (B) of FIG. 14, high contrast can be achieved even with the objective lens of the dry type.

Feature 2 is extremely effective in acquisition of the quantitative phase image. In acquisition of the quantitative phase image, variation in height of the liquid surface due to vibration of the solution leads to variation in optical path length, so as to produce noise in measurement. For this reason, measurement is preferably carried out while keeping the height of the liquid surface unchanged. In performing observation without interruption, however, there are cases where a medical fluid is dispensed in the middle and a change thereafter is measured, and in such cases the dispensation of medical fluid inevitably causes vibration of the liquid surface. Therefore, the fifth example is characterized by the top part (or lid) of the vessel 102A housing the cells 101.

Namely, the upper part (or lid) of the vessel 102A is provided with the observation window 116 such as glass parallel to such a height as to contact the culture solution 115, so as to keep the height of the culture solution 115 constant. Thanks to the existence of the observation window 116, the height of the solution in the observation region of the vessel 102A housing the cells 101 is kept constant between the bottom surface of the vessel 102A as an observation surface in contact with the cells 101 and the observation window 116 in the upper part of the vessel 102A. The observation window 116 is provided in the range corresponding to the observation region of the bottom surface of the vessel 102A and an aperture is formed in the periphery to allow the dispensation of medical fluid. In acquisition of the quantitative phase image, the observation window 116 is preferably parallel to the bottom surface of the sample. When the observation window 116 to keep the height of the culture solution 115 constant is provided in contact with the culture solution 115 in the upper part of the vessel 102A, the quantitative phase image is stable in terms of time and the measurement result of optical path lengths of cells 101 can be always obtained under the stable condition. The observation window 116 in the upper part of the vessel 102A also serves as a lid of the vessel 102A and it is feasible to maintain the inside in an aseptic condition with the lid closed. With consideration to the dispensation of medical fluid, the lid part may be provided with an aperture for the dispensation of medical fluid.

Feature 3 is provision of the antireflection coat 117 on the observation window 116 outside the vessel 102A (or on the air side opposite to the surface in contact with the culture solution 115), for acquisition of the reflection interference image. Without the antireflection coat 117, the difference is large between the refractive indices of the glass of the observation window 116 in contact with the solution above the cells 101 and the exterior air and the illumination light from the objective lens for the purpose of acquisition of the reflection interference image is reflected approximately 4% on the observation window 116. The reflected light illuminates the cells 101 to project a contour image of cells 101 onto the reflection interference image. This is information obstructive to extraction of the information limited to the adhesion faces from the reflection interference image and inhibits acquisition of a clear reflection interference image. In the fifth example, therefore, the antireflection coat to control the reflectance to about 0.5% in the wavelength range of the illumination light is provided on the observation window 116 outside the vessel 102A, whereby the reflectance can be reduced to about ⅛. This suppresses the influence of reflected light from the top surface, whereby the reflection interference image of the cell adhesion faces can be obtained with high contrast.

FIG. 15 shows an improvement of the reflection interference image in the case where the antireflection coat 117 is provided on the observation window 116 in the upper part of the vessel 102A. Without the treatment, as shown in (A) of FIG. 15, the reflected light from the interface between the observation window 116 in the upper part of the vessel 102A and air illuminates the cells 101 from the top to project a contour image of cells 101 onto the image. On the other hand, when the antireflection coat 117 is provided on the air side of the observation window 116 in the upper part, as shown in (B) of FIG. 15, the reflection from the top is reduced, whereby the reflection interference image of the adhesion faces of cells 101 can be observed with good contrast.

Figure 16:
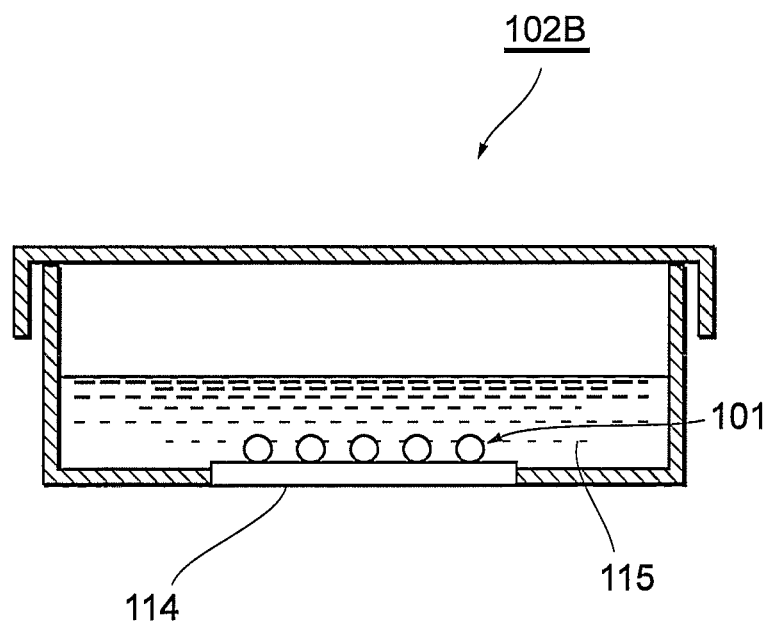
FIG. 16 is a drawing showing a modification example of the fifth example.

If stationary-standing observation is carried out, for example, in a state in which no medical fluid or the like is dispensed during measurement, so as to prevent disturbance of the culture solution 115 in the vessel 102A housing the cells 101, the provision of the foregoing observation window 116 is not essential, and the vessel may be vessel 102B having only feature 1 with the antireflection coat 114 on the bottom surface of the vessel, as shown in FIG. 16.

[Sixth Example]

The sixth example of the present invention will be described below. The sixth example is different in the image acquisition unit 10, out of the constituent elements of the first example shown in FIG. 1. Namely, the present example is characterized by the configuration of the optical system for simultaneously carrying out the quantitative phase measurement and the reflection interference measurement.

Figure 17:
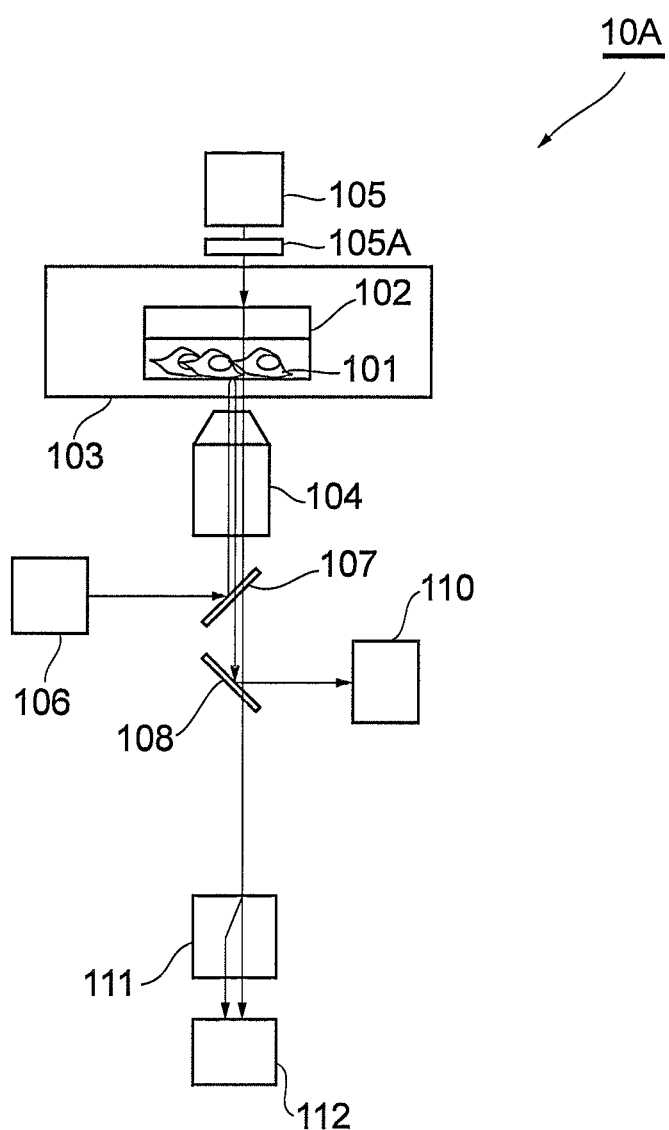
FIG. 17 is a drawing showing an image acquisition unit 10A in a sixth example.

FIG. 17 shows an image acquisition unit 10A in the sixth example. When compared with the image acquisition unit 10 in the first example, the image acquisition unit 10A is configured without use of the total reflection mirror 109. Namely, the quantitative phase optical system consists of only the diffractive interference optical system 111. This configuration can substantialize the simple configuration and provides the advantage of being easy to construct the device.

In the quantitative phase measurement, the illumination light emitted from the quantitative phase measurement light source 105 installed above the vessel 102 housing the cells 101 travels through the vessel 102 housing the cells 101, to be condensed by the objective lens 104. Then the illumination light travels through the half mirror 107 and then through the dichroic mirror 108 for separation of the quantitative phase image and the reflection interference image by wavelengths, to form an interference image between object light and reference light in the diffractive interference optical system 111 for phase measurement, and the interference fringe image is taken by the quantitative phase detection camera 112.

In the reflection interference measurement, the illumination light emitted from the reflection interference measurement light source 106 is reflected by the half mirror 107, then travels through the objective lens 104, and is incident into the vessel 102 housing the cells 101 as a measurement target, from the bottom side. Reflected light from the adhesion faces of cells 101 on the bottom surface of the vessel 102 causes interference according to the adhesion distances of the cells 101, the resultant reflection interference light is condensed by the objective lens 104, the light travels through the half mirror 107, and only the reflection interference image is reflected by the dichroic mirror 108 for separation of the quantitative phase image and the reflection interference image by wavelengths, to be picked up by the reflection interference detection camera 110.

[Seventh Example]

The seventh example of the present invention will be described below. The seventh example is different in the image acquisition unit 10, out of the constituent elements of the first example shown in FIG. 1. Namely, the present example is characterized by the configuration of the optical system for simultaneously performing the quantitative phase measurement and the reflection interference measurement.

Figure 18:
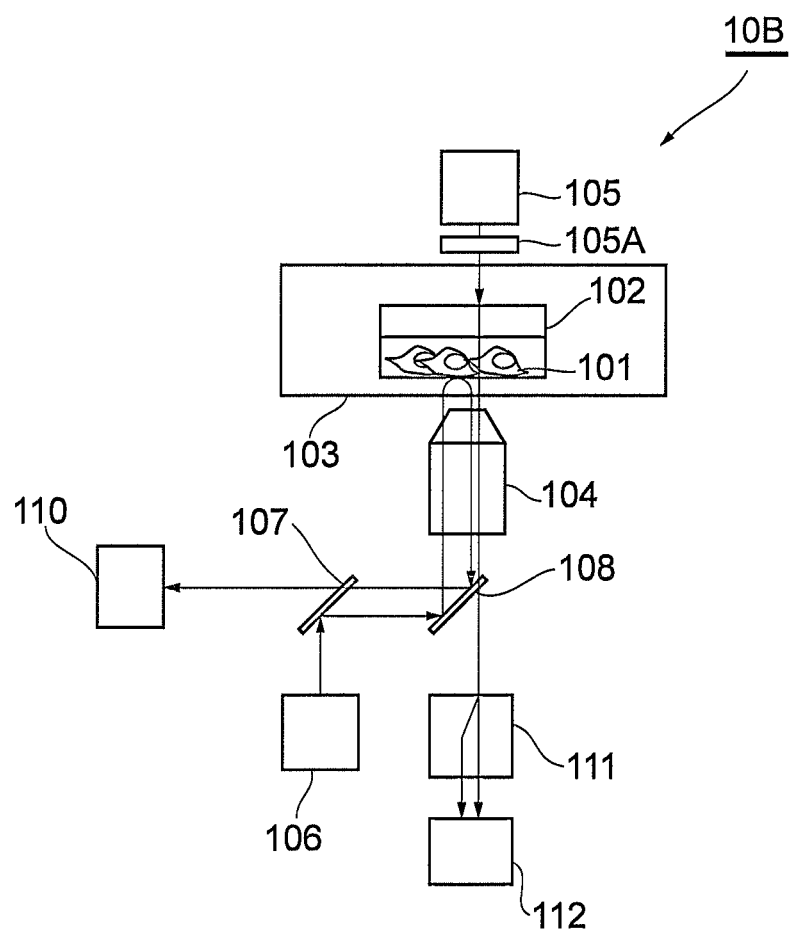
FIG. 18 is a drawing showing an image acquisition unit 10B in a seventh example.

FIG. 18 shows an image acquisition unit 10B in the seventh example. When compared with the image acquisition unit 10 in the first example, the image acquisition unit 10B is configured without use of the total reflection mirror 109. Therefore, the present example can realize the simple configuration and has the advantage of being easy to construct the device. Since the half mirror 107 of the reflection interference incidence optical system is not a common optical system, the quantitative phase image is taken without passage through the half mirror 107, thereby providing the advantage of reduction in light quantity loss on the quantitative phase side.

In the quantitative phase measurement, the illumination light emitted from the quantitative phase measurement light source 105 installed above the vessel 102 housing the cells 101 travels through the vessel 102 housing the cells 101, to be condensed by the objective lens 104. Then, without passing through the half mirror 107, the illumination light travels through the dichroic mirror 108 for separation of the quantitative phase image and the reflection interference image by wavelengths, to form the interference image between object light and reference light in the diffractive interference optical system 111 for phase measurement, and the interference fringe image is taken by the quantitative phase detection camera 112.

In the reflection interference measurement, the illumination light emitted from the reflection interference measurement light source 106 is reflected by the half mirror 107 and the dichroic mirror 108, then travels through the objective lens 104, and is incident into the vessel 102 housing the cells 101 as a measurement target, from the bottom side. Reflected light from the adhesion faces of the cells 101 on the bottom surface of the vessel 102 causes interference according to the adhesion distances of the cells 101, the resultant reflection interference light is condensed by the objective lens 104, and then the light travels again via the dichroic mirror 108 and the half mirror 107 to be picked up by the reflection interference detection camera 110.

[Eighth Example]

The eighth example of the present invention will be described below. The eighth example is different in the image acquisition unit 10, out of the constituent elements of the first example shown in FIG. 1. Namely, the present example is characterized by the configuration of the optical system for simultaneously performing the quantitative phase measurement and the reflection interference measurement.

Figure 19:
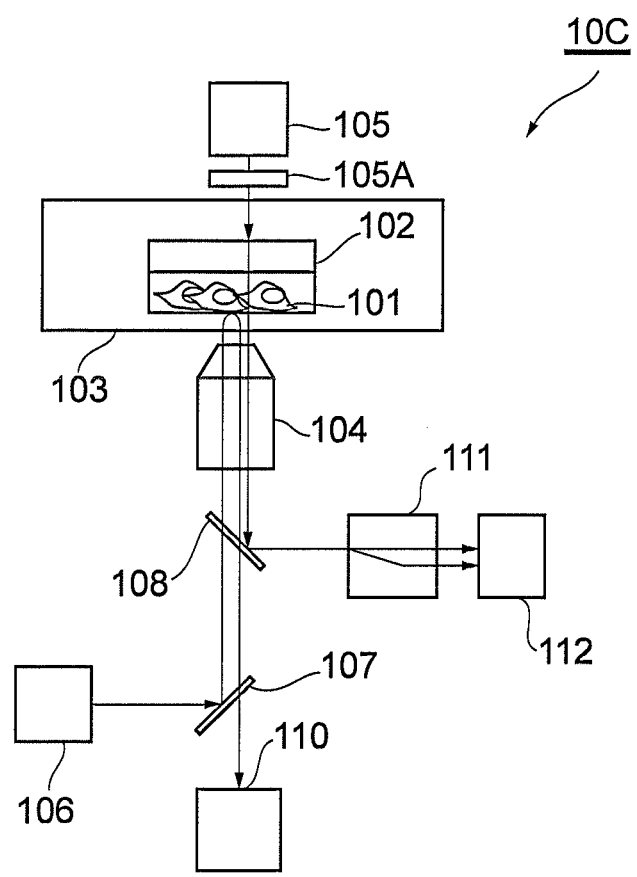
FIG. 19 is a drawing showing an image acquisition unit 10C in an eighth example.

FIG. 19 shows an image acquisition unit 10C in the eighth example. When compared with the image acquisition unit 10 in the first example, the image acquisition unit 10C is configured without use of the total reflection mirror 109. Namely, the quantitative phase optical system consists of only the diffractive interference optical system 111, thus realizing the simple configuration and providing the advantage of being easy to construct the device. Since the half mirror 107 of the reflection interference incidence optical system is not a common optical system, the quantitative phase image is taken without passing through the half mirror 107, thereby providing the advantage of reduction in light quantity loss on the quantitative phase side.

In the quantitative phase measurement, the illumination light emitted from the quantitative phase measurement light source 105 installed above the vessel 102 housing the cells 101 travels through the vessel 102 housing the cells 101, to be condensed by the objective lens 104. Then, without passing through the half mirror 107, the illumination light is reflected from the dichroic mirror 108 for separation of the quantitative phase image and the reflection interference image by wavelengths, to form the interference image between object light and reference light in the diffractive interference optical system 111 for phase measurement, and the interference fringe image is taken by the quantitative phase detection camera 112.

In the reflection interference measurement, the illumination light emitted from the reflection interference measurement light source 106 is reflected via the half mirror 107 and the dichroic mirror 108, travels through the objective lens 104, and is then incident into the vessel 102 housing the cells 101 as a measurement target, from the bottom side. Reflected light from the adhesion faces of the cells 101 on the bottom surface of the vessel 102 causes interference according to the adhesion distances of the cells 101, the resultant reflection interference light is condensed by the objective lens 104, and then the light travels again via the dichroic mirror 108 and the half mirror 107 to be picked up by the reflection interference detection camera 110.

[Ninth Example]

The ninth example of the present invention will be described below. The ninth example is different in the image acquisition unit 10, out of the constituent elements of the first example shown in FIG. 1. Namely, the present example is characterized by the configuration of the optical system for simultaneously performing the quantitative phase measurement and the reflection interference measurement.

Figure 20:
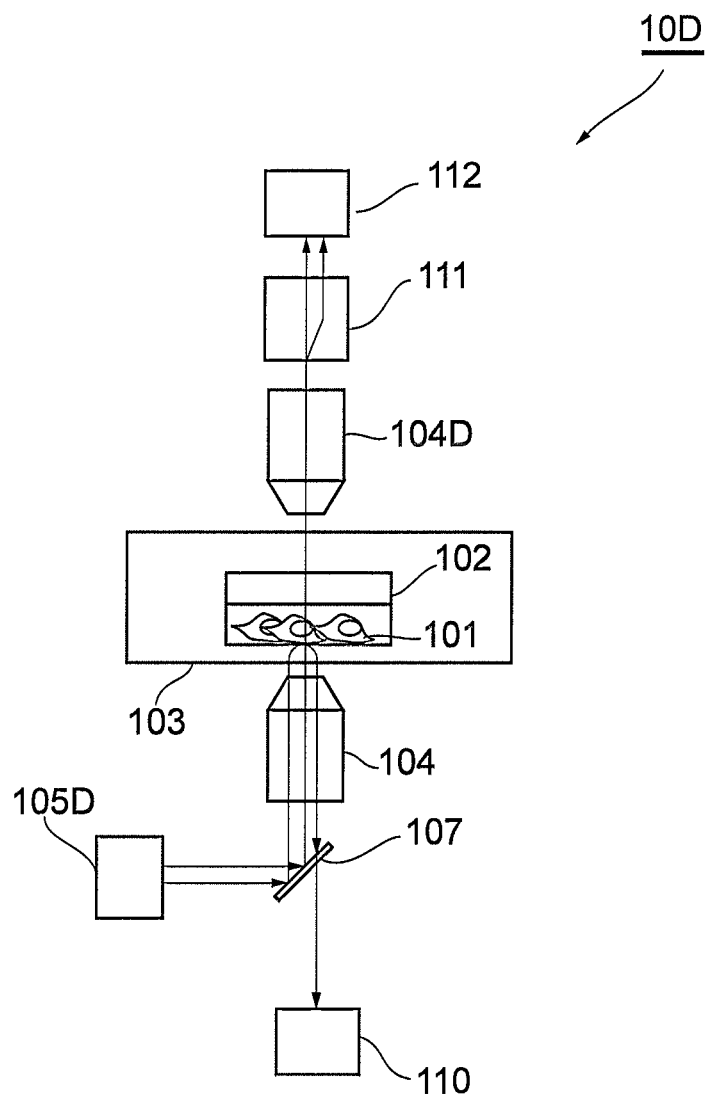
FIG. 20 is a drawing showing an image acquisition unit 10D in a ninth example.

FIG. 20 shows an image acquisition unit 10D in the ninth example. When compared with the image acquisition unit 10 in the first example, the image acquisition unit 10D is configured without use of the total reflection mirror 109 and the dichroic mirror 108, and has one common light source 105D instead of the quantitative phase measurement light source 105 and the reflection interference measurement light source 106. Therefore, the present example can realize the simple configuration and provides the advantage of being easy to construct the device. However, the present example needs to have a second objective lens 104D.

In the quantitative phase measurement, the illumination light emitted from the common light source 105D is reflected by the half mirror 107, then travels through the objective lens 104, passes through the vessel 102 housing the cells 101, and is condensed by the second objective lens 104D. Then the interference image between object light and reference light is formed in the diffractive interference optical system 111 and the interference fringe image is taken by the quantitative phase detection camera 112.

In the reflection interference measurement, the illumination light emitted from the common light source 105D is reflected by the half mirror 107, travels through the objective lens 104, and is incident into the vessel 102 housing the cells 101 as a measurement target, from the bottom side. The reflected light from the adhesion faces of the cells 101 on the bottom surface of the vessel 102 causes interference according to the adhesion distances of the cells 101, the resultant reflection interference light is condensed by the objective lens 104, and the light travels again via the half mirror 107 to be picked up by the reflection interference detection camera 110.

[Tenth Example]

The tenth example of the present invention will be described below. The tenth example is different in the image acquisition unit 10, out of the constituent elements of the first example shown in FIG. 1. Namely, the present example is characterized by the configuration of the optical system for simultaneously performing the quantitative phase measurement and the reflection interference measurement.

Figure 21:
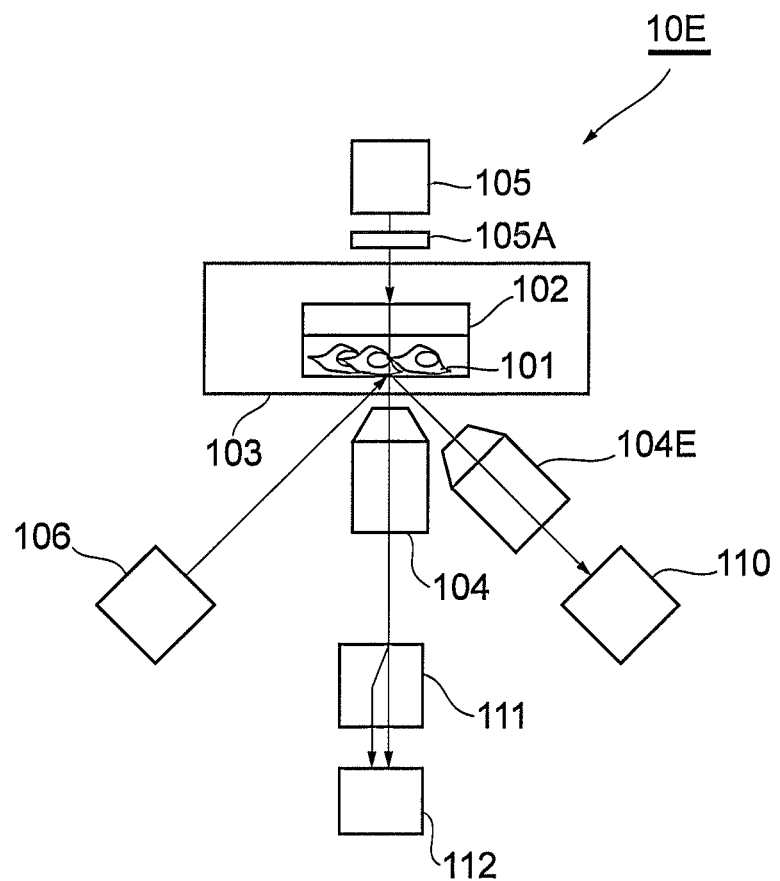
FIG. 21 is a drawing showing an image acquisition unit 10E in a tenth example.

FIG. 21 shows an image acquisition unit 10E in the tenth example. When compared with the image acquisition unit 10 in the first example, the image acquisition unit 10E is configured without use of the total reflection mirror 109, the half mirror 107, and the dichroic mirror 108 and, the light beam for quantitative phase measurement and the light beam for reflection interference measurement are separated by angles instead of wavelengths. The present example needs to have a second objective lens 104E.

In the quantitative phase measurement, the illumination light emitted from the quantitative phase measurement light source 105 installed above the vessel 102 housing the cells 101 travels through the vessel 102 housing the cells 101, to be condensed by the objective lens 104. Then, without passing via the half mirror 107 and the dichroic mirror 108, the interference image between object light and reference light is formed in the diffractive interference optical system 111 and the interference fringe image is taken by the quantitative phase detection camera 112.

In the reflection interference measurement, the illumination light emitted from the reflection interference measurement light source 106 is obliquely incident into the vessel 102 housing the cells 101 as a measurement target, from the bottom side. The reflected light from the adhesion faces of the cells 101 on the bottom surface of the vessel 102 causes interference according to the adhesion distances of the cells 101, the resultant reflection interference light travels again obliquely through the second objective lens 104E to be condensed thereby, and then the light travels without passing via the half mirror 107 or the dichroic mirror 108, to be picked up by the reflection interference detection camera 110. The present example requires adjustment of angles among the reflection interference measurement light source 106, the second objective lens 104E, and the reflection interference detection camera 110, but can be configured without use of the total reflection mirror 109, half mirror 107, and dichroic mirror 108, thus providing the advantage of implementation of the simple configuration.

[Eleventh Example]

The eleventh example of the present invention will be described below. The eleventh example is different in the image acquisition unit 10, out of the constituent elements of the first example shown in FIG. 1. Namely, the present example is characterized by the configuration of the optical system for simultaneously performing the quantitative phase measurement and the reflection interference measurement.

Figure 22:
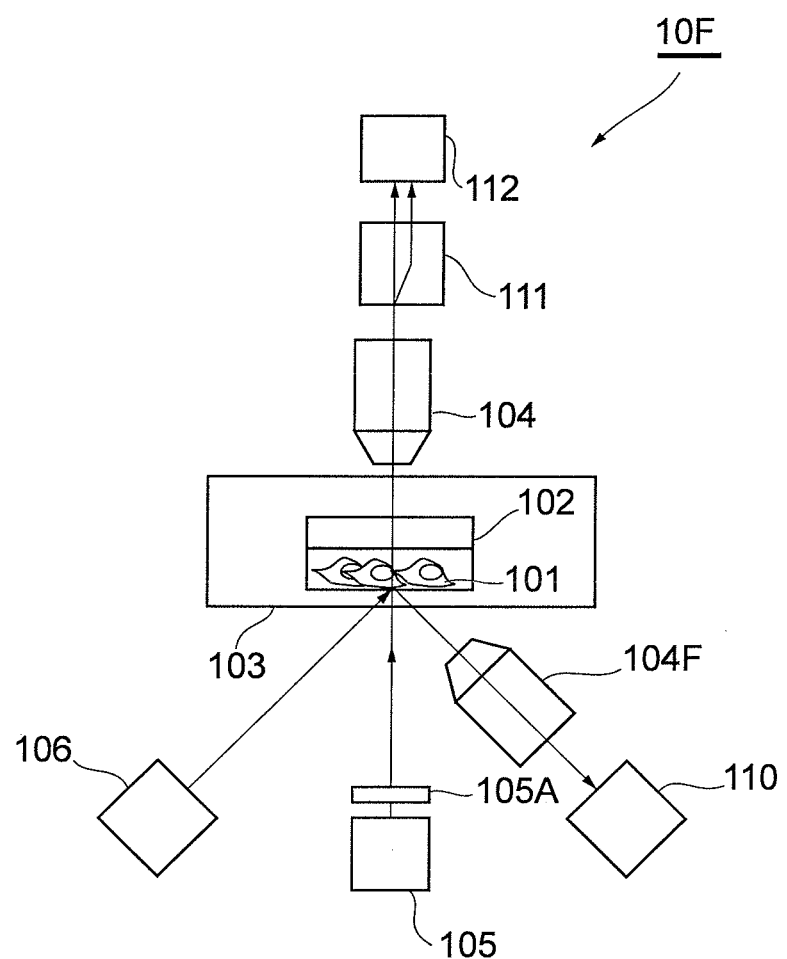
FIG. 22 is a drawing showing an image acquisition unit 10F in an eleventh example.

FIG. 22 shows an image acquisition unit 10F in the eleventh example. When compared with the image acquisition unit 10 in the first example, the image acquisition unit 10F is configured without use of the total reflection mirror 109, the half mirror 107, and the dichroic mirror 108 and, the light beam for quantitative phase measurement and the light beam for reflection interference measurement are separated by angles instead of wavelengths. The present example needs to have a second objective lens 104F.

In the quantitative phase measurement, the illumination light emitted from the quantitative phase measurement light source 105 is incident into the vessel 102 housing the cells 101 as a measurement target, from the bottom side. The illumination light travels through the vessel 102 housing the cells 101, to be condensed by the objective lens 104. Then, without passing via the total reflection mirror 109, the half mirror 107, or the dichroic mirror 108, the interference image between object light and reference light is formed in the diffractive interference optical system 111 and the interference fringe image is taken by the quantitative phase detection camera 112.

In the reflection interference measurement, the illumination light emitted from the reflection interference measurement light source 106 is obliquely incident into the vessel 102 housing the cells 101 as a measurement target, from the bottom side. The reflected light from the adhesion faces of the cells 101 on the bottom surface of the vessel 102 causes interference according to the adhesion distances of the cells 101, the resultant reflection interference light travels again obliquely through the second objective lens 104F to be condensed thereby, and the light travels without passing via the total reflection mirror 109, the half mirror 107, or the dichroic mirror 108, to be picked up by the reflection interference detection camera 110. The present example requires adjustment of angles among the reflection interference measurement light source 106, the second objective lens 104F, and the reflection interference detection camera 110, but can be configured without use of the total reflection mirror 109, the half mirror 107, and the dichroic mirror 108, thereby providing the advantage of implementation of the simple configuration.

[Twelfth Example]

The twelfth example of the present invention will be described below. The twelfth example is different in the image acquisition unit 10, out of the constituent elements of the first example shown in FIG. 1. Namely, the present example is characterized by the configuration of the optical system for simultaneously performing the quantitative phase measurement and the reflection interference measurement and, specifically, the quantitative phase measurement method is modified into a two-beam system.

Figure 23:
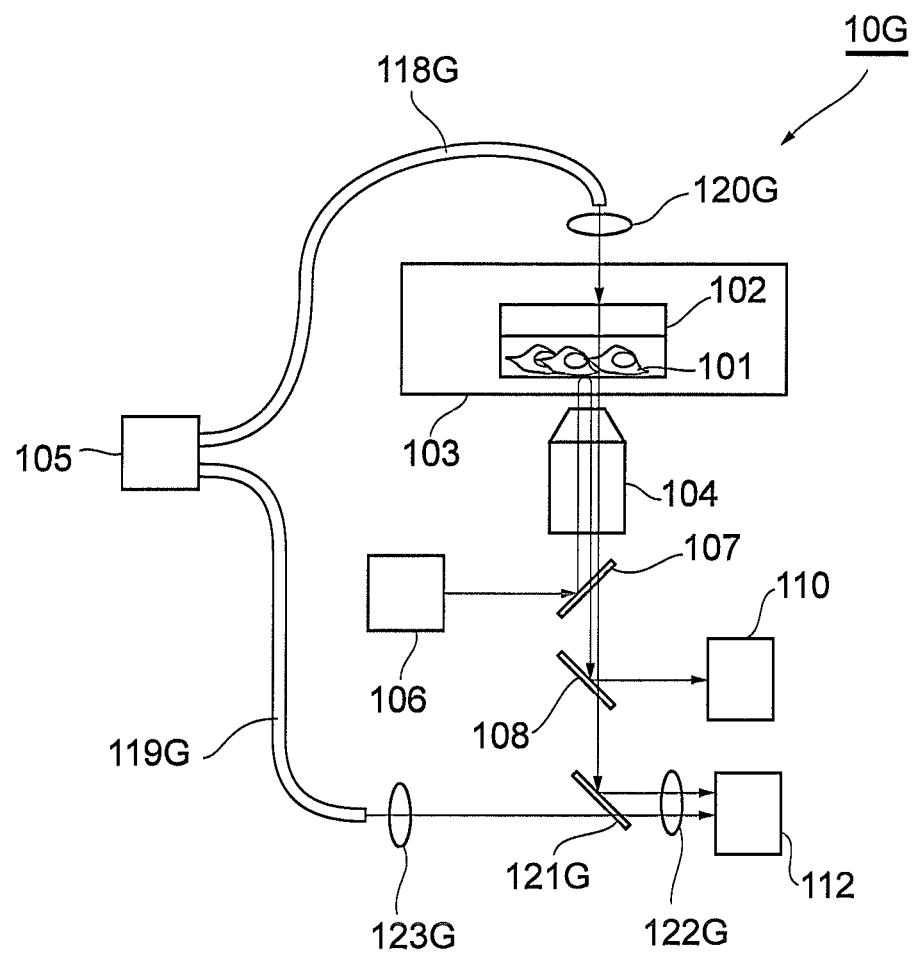
FIG. 23 is a drawing showing an image acquisition unit 10G in a twelfth example.

FIG. 23 shows an image acquisition unit 10G in the twelfth example. When compared with the image acquisition unit 10A in the sixth example, the image acquisition unit 10G is different in that, without use of the diffractive interference optical system 111, illumination and reference light beams from the quantitative phase measurement light source 105 are guided through respective optical paths 118G and 119G to the quantitative phase detection camera 112. The present example provides the advantage of being capable of constructing the device without the diffractive interference optical system 111. The present example is configured by adopting the two-beam system, instead of use of the diffractive interference optical system 111, as the quantitative phase measurement method, so as to produce the reference light beam through the separate optical path, and finally making the object beam and the reference beam interfere with each other.

In the quantitative phase measurement, the illumination light from the quantitative phase measurement light source 105 travels through the optical path 118G for illumination light, then travels through a lens 120G installed above the vessel 102, passes through the cells 101 in the vessel 102, and is condensed by the objective lens 104. Then the light travels via the half mirror 107, passes through the dichroic mirror 108, and further travels via a half mirror 121G and a lens 122G to reach the quantitative phase detection camera 112. On the other hand, the reference beam from the quantitative phase measurement light source 105 travels through the optical path 119G for the reference beam, and then travels in order through a lens 123G, the half mirror 121G, and the lens 122G to reach the quantitative phase detection camera 112.

In the reflection interference measurement, the illumination light emitted from the reflection interference measurement light source 106 is reflected by the half mirror 107, travels through the objective lens 104, and is incident into the vessel 102 housing the cells 101 as a measurement target, from the bottom side. The reflected light from the adhesion faces of the cells 101 on the bottom surface of the vessel 102 causes interference according to the adhesion distances of the cells 101, the resultant reflection interference light is condensed again by the objective lens 104, and travels via the half mirror 107, and only the reflection interference image is reflected by the dichroic mirror 108 for separation of the quantitative phase image and the reflection interference image by wavelengths, to be picked up by the reflection interference detection camera 110.

[Thirteenth Example]

The thirteenth example of the present invention will be described below. The thirteenth example is different in the image acquisition unit 10, out of the constituent elements of the first example shown in FIG. 1. Namely, the present example is characterized by the configuration of the optical system for simultaneously performing the quantitative phase measurement and the reflection interference measurement.

Figure 24:
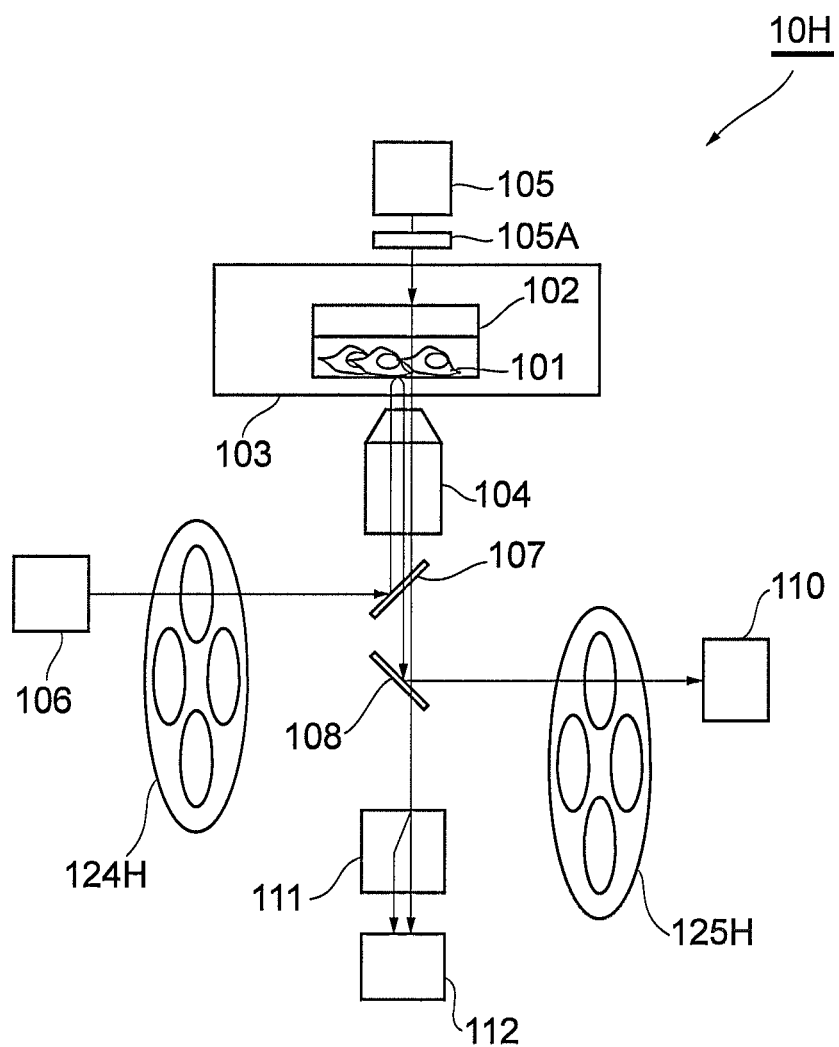
FIG. 24 is a drawing showing an image acquisition unit 10H in a thirteenth example.

FIG. 24 shows an image acquisition unit 10H in the thirteenth example. When compared with the image acquisition unit 10A in the sixth example, the image acquisition unit 10H is different in that it is further provided with an illumination wavelength switch device 124H and an observation wavelength switch device 125H. The illumination wavelength switch device 124H is a device that switches the wavelengths of the illumination light from the reflection interference measurement light source 106 to other wavelengths. The observation wavelength switch device 125H is a device that switches the wavelengths of the observation light from the dichroic mirror 108 to other wavelengths. Since the image acquisition unit 10H is provided with these devices, it is able to acquire a desired fluorescence image or the like by the reflection interference detection camera 110. FIG. 24 shows the illumination wavelength switch device 124H and the observation wavelength switch device 125H configured to perform switching of wavelengths by rotation, as an example.

In the quantitative phase measurement, the illumination light emitted from the quantitative phase measurement light source 105 installed above the vessel 102 housing the cells 101, travels through the vessel 102 housing the cells 101, to be condensed by the objective lens 104. Then the light travels via the half mirror 107, passes through the dichroic mirror 108 for separation of the quantitative phase image and the reflection interference image by wavelengths, to form the interference image between object light and reference light in the diffractive interference optical system 111 for phase measurement, and the interference fringe image is taken by the quantitative phase detection camera 112.

In the reflection interference measurement, the illumination light emitted from the reflection interference measurement light source 106 is switched to desired wavelengths by the illumination wavelength switch device 124H, and the light is reflected by the half mirror 107, travels through the objective lens 104, and is then incident into the vessel 102 housing the cells 101 as a measurement target, from the bottom side. The reflected light from the adhesion faces of the cells 101 on the bottom surface of the vessel 102 causes interference according to the adhesion distances of the cells 101, the resultant reflection interference light is condensed by the objective lens 104, the light travels again via the half mirror 107, only the reflection interference image is reflected by the dichroic mirror 108, and the reflected light is switched into desired wavelengths by the observation wavelength switch device 125H, to be picked up by the reflection interference detection camera 110.

[Fourteenth Example]

The fourteenth example of the present invention will be described below. The fourteenth example is different in the half mirror 107, out of the constituent elements of the first example shown in FIG. 1. Namely, the fourteenth example includes all the constituent elements of the first embodiment, of which the characteristics of the half mirror 107 are further improved.

Figure 25:
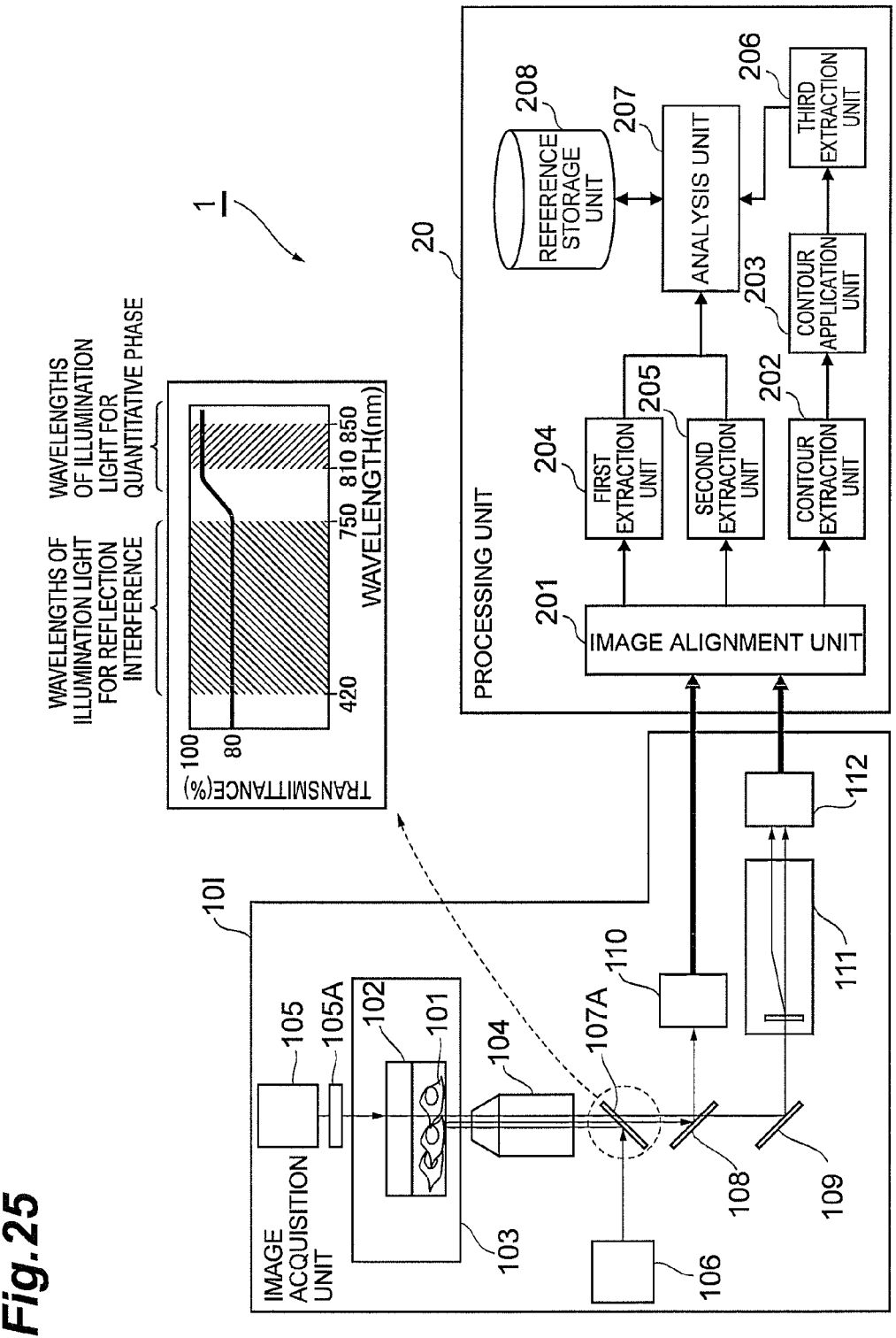
FIG. 25 is a drawing showing an image acquisition unit 10I in a fourteenth example.

An ordinary half mirror generally has an equal separation ratio throughout the entire wavelength zone. If such a half mirror is used as the half mirror 107 in the present embodiment, the transmittance of the quantitative phase image will be limited by the half mirror 107 when the quantitative phase image passes through the half mirror 107 placed in the optical path for the purpose of reflection interference. Then the fourteenth example employs a half mirror 107A which is located between the reflection interference measurement light source 106 and the camera 110 and between the quantitative phase measurement light source 105 and the camera 110 and which can have different ratios of reflection to transmittance depending upon wavelengths, as shown in an image acquisition unit 10I in FIG. 25. The fourteenth example is based on the premise that the quantitative phase measurement light source 105 and the reflection interference measurement light source 106 emit their respective illumination beams of different wavelengths, so as to avoid an overlap between the wavelengths of the illumination beams for reflection interference and quantitative phase. The wavelength characteristics of the half mirror 107A are such wavelength characteristics that it works as a half mirror (transmission:reflection=80:20 in FIG. 25) in the observation wavelength region of reflection interference and it transmits maximum light in the observation wavelength region of quantitative phase. This configuration decreases a loss in light quantity of the observation light for quantitative phase.

For example, in a case where the visible light (420 nm to 750 nm) is used in reflection interference and light with the center wavelength of 830 nm and the full width at half maximum of 20 nm is used in quantitative phase, the wavelength characteristics of the half mirror 107A are set so that the ratio of reflection:transmission is set at 20:80 for the visible light (420 nm to 750 nm) and the ratio of reflection:transmission is set at 5:95 for 800 nm and above. This setup allows 80% of observation light to be obtained for the reflection interference and allows a signal to be obtained at the transmittance of 95% for quantitative phase, independent of the transmittance in the reflection interference of the half mirror 107A.

[Fifteenth Example]

The fifteenth example of the present invention will be described below. The fifteenth example has the same configuration as the configuration of the first example shown in FIG. 1, but may be configured without the reference storage unit 208 in FIG. 1, though not shown, because the analysis unit 207 performs the processing without depending on the reference storage unit 208.

In the fifteenth example, the analysis unit 207 determines a type or state of a cell as an unknown specimen, independently of the reference data. Namely, the analysis unit 207 selects predetermined parameters from the parameters extracted for the unknown cell and determines the type or state of unknown cell, using the predetermined parameters thus selected. The analysis unit 207 may be configured so as to automatically select parameters indicative of peculiar values as the predetermined parameters. A separate processing means may be provided in order to perform the parameter selection process. On the other hand, the analysis unit 207 may be configured to select the predetermined parameters, based on an input from the user.

Figure 26:
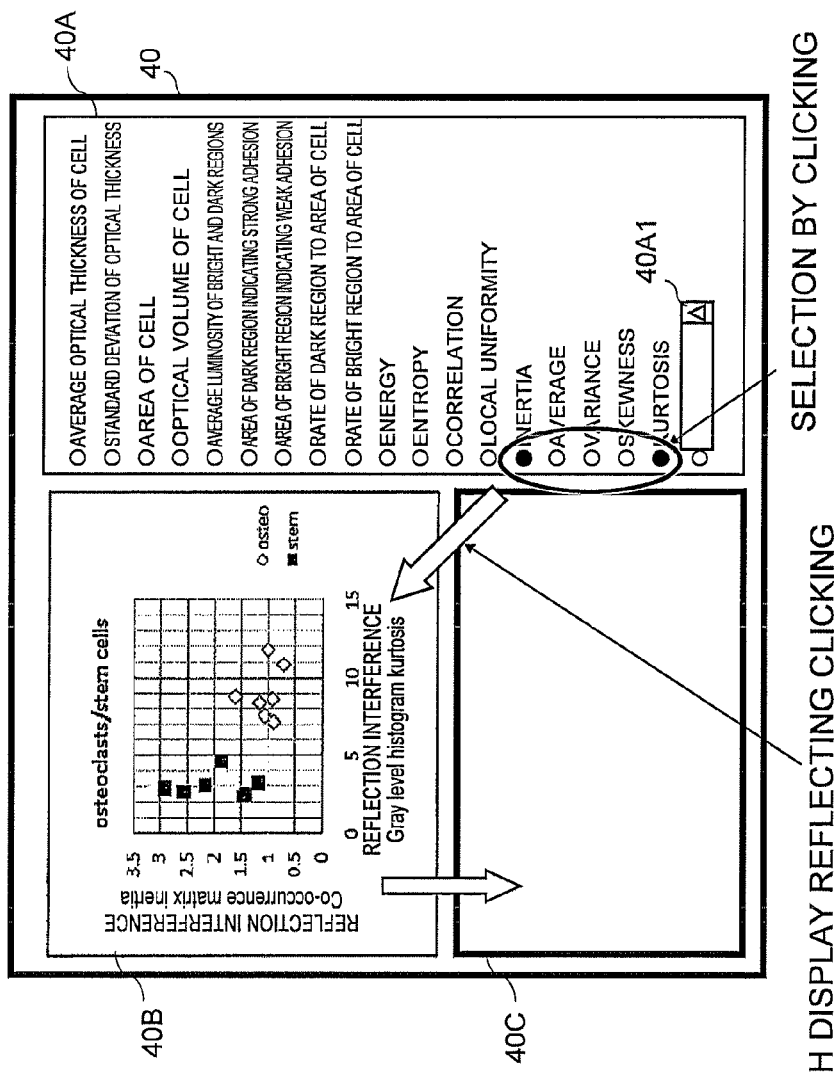
FIG. 26 is a drawing showing an example of a screen displayed for a user in a fifteenth example.

FIG. 26 shows a screen 40 displayed for the user, in the configuration wherein the analysis unit 207 is configured to select the predetermined parameters, based on the input from the user, in the fifteenth example. A screen field 40A is a picture that shows kinds of parameters for the user and that is provided for accepting selection by the user. In the example of the screen field 40A, the user selects the inertia and kurtosis as the predetermined parameters. The user may be allowed to use a selection tool 40A1 or the like to select other parameters not displayed on the screen field 40A. A screen field 40B shows an example of display on a graph reflecting the parameters selected by the user. After the user checks the screen field 40B, the user may return to the screen field 40A to select other parameters, or may advance directly to a screen field 40C. The screen field 40C is a picture displaying an image of the cell.

In the fifteenth example of this configuration, the analysis unit 207 can perform the processing, without depending upon the reference data. Therefore, the reference storage unit 208 may be omitted, which simplifies the device configuration. This mode of embodiment is suitably applicable, for example, to the case where it is known in advance that the cells in the sample are separated into myeloid stem cells and osteoclasts and where the cells are to be discriminated from each other.

[Sixteenth Example]

The sixteenth example of the present invention will be described below. The sixteenth example is different mainly in the operation of the analysis unit 207, out of the constituent elements of the first example shown in FIG. 1. The sixteenth example is based on the premise that three or more parameters are extracted by each of the first extraction unit 204, the second extraction unit 205, and the third extraction unit 206, or by a combination thereof, and in this case the analysis unit 207 performs a principal component analysis on the three or more parameters to determine a type or state of an unknown cell.

The operation in the sixteenth example is briefly summarized as follows. First, three or more parameters are extracted by each of the first extraction unit 204, the second extraction unit 205, and the third extraction unit 206, or by a combination thereof and are output to the analysis unit 207 (hereinafter "step 1"). Next, the analysis unit 207 standardizes the three or more parameters (hereinafter "step 2"). Next, the analysis unit 207 determines a first principal component and a second principal component, based on the standardized data (hereinafter "step 3"). Then the analysis unit 207 plots cells on a two-component scatter diagram of the first principal component and the second principal component and performs cell determination (hereinafter "step 4"). Each of the steps will be detailed below based on an actual experiment example.

(Step 1: Parameter Extraction)

In this experiment, four types of cells, each type including ten cells, were used as reference and three unknown cells were discriminated based thereon. The experiment was conducted based on the assumption that the three unknown cells were included in any one of the four types of cells, and the purpose of the experiment is to discriminate the three unknown cells as to in which they are included among the four types of cells. The below provides the names, notations, and numbers (n) of the respective cells used as reference, in order.

Rat pancreatic β cell line INS-1 (n=10)
Mouse pancreatic β cell line MIN-6 (n=10)
Human pancreatic cancer cell line MIAPaCa-2 (n=10)
Human uterine cervix cancer cell line HeLa (n=10)

Figure 27:
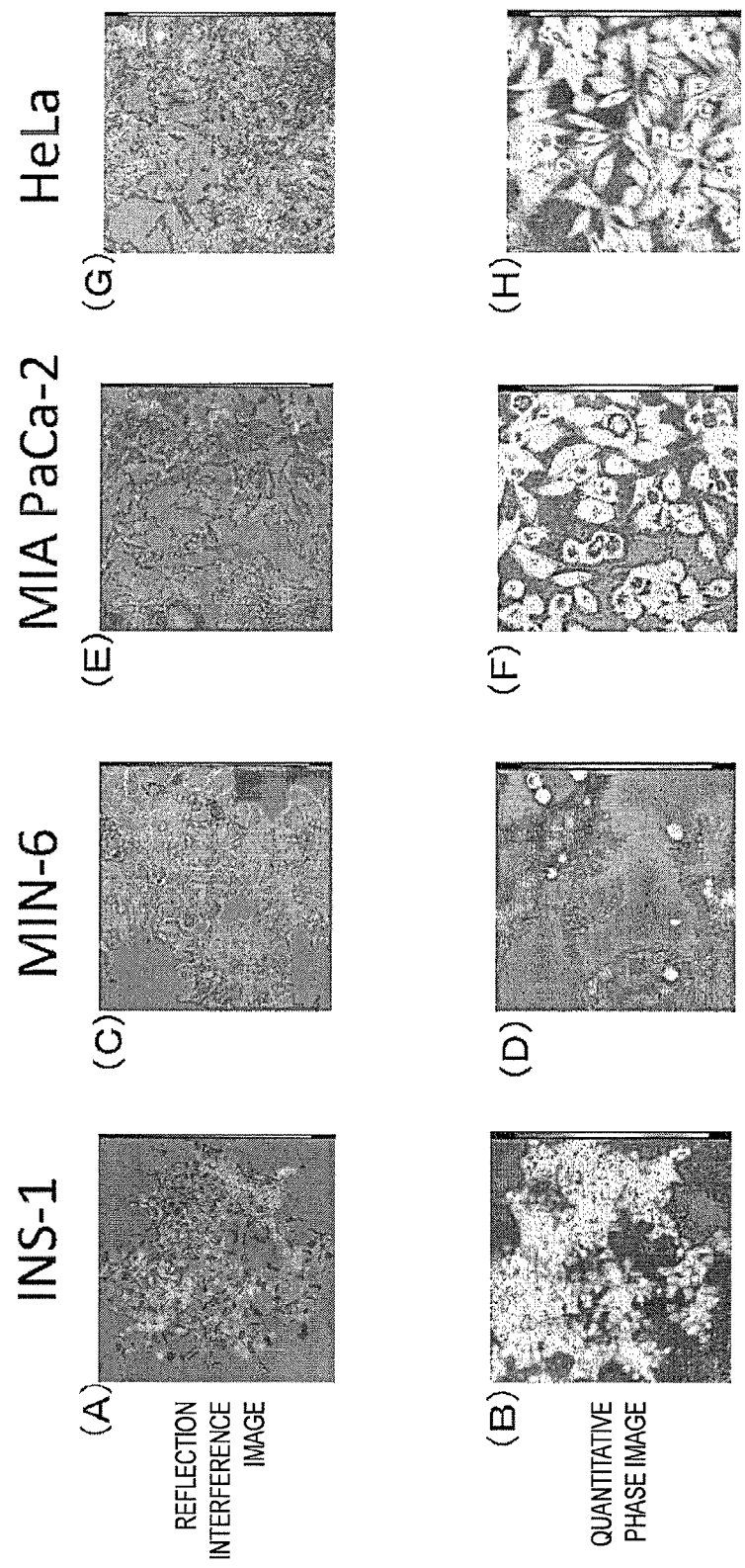
FIG. 27 is a drawing showing reflection interference images and quantitative phase images of respective cells used as reference, in a sixteenth example.

FIG. 27 shows the reflection interference images and quantitative phase images of the respective cells used as reference. (A) and (B) in FIG. 27 show the reflection interference image and quantitative phase image of rat pancreatic β cell line (INS-1) in order. (C) and (D) in FIG. 27 show the reflection interference image and quantitative phase image of mouse pancreatic β cell line (MIN-6) in order. (E) and (F) in FIG. 27 show the reflection interference image and quantitative phase image of human pancreatic cancer cell line (MIAPaCa-2) in order. (G) and (H) in FIG. 27 show the reflection interference image and quantitative phase image of human uterine cervix cancer cell line (HeLa) in order.

In this experiment, each of the first extraction unit 204, the second extraction unit 205, and the third extraction unit 206, or a combination thereof extracted seven parameters below from the reflection interference images and quantitative phase images shown in FIG. 27. The parameters (1) and (2) below are parameters obtained from the quantitative phase images and the parameters (3) to (7) parameters obtained from the reflection interference images. FIG. 28 shows actually measured values of the seven parameters.

(1) Area of cell
(2) Thickness of cell
(3) Texture of adhesion face: co-occurrence matrix/local uniformity
(4) Texture of adhesion face: co-occurrence matrix/inertia
(5) Contrast of adhesion face: gray level histogram/skewness
(6) Contrast of adhesion face: gray level histogram/kurtosis
(7) Contrast of adhesion face: gray level histogram/(variance)/average (Step 2: Standardization)

For obtaining components indicative of summarized features (principal components) from the plurality of parameters extracted in above step 1, it is necessary to create a linear formula including the parameters. However, the measured values shown in FIG. 28 are represented by different units depending on the parameters, and the magnitudes of taken values are different from each other. If these values are handled as they are, information will be biased to parameters of large values and it will be difficult to equally extract information from each of the parameters. Then an amount of information of each parameter was calculated in order to equally extract information from each parameter. As an information amount, the sum of squared deviations from a population was calculated from the measured values shown in FIG. 28 and then the calculation result as shown in FIG. 29 was obtained. However, there were large differences of information amounts among the parameters, as shown in FIG. 29. Since it is desirable to equalize the information amounts of the respective parameters, the present experiment adopted standardization of data, based on formula (1) below, for each of the parameters.

$$X' = (Xi - X)/Xsd \qquad (1)$$

In formula (1), X' is data after standardization, Xi each measured value shown in FIG. 28, X an average value in Xi, and Xsd a standard deviation in Xi.

FIG. 30 shows values of the respective parameters after the standardization. As shown in FIG. 30, as the result of standardization, the information amounts of the respective parameters are equal independent of the types of parameters. When such data after standardization is used, the data can be handled equally.

(Step 3: Calculation of Principal Components)

Next, the analysis unit 207 obtains the first principal component f and the second principal component g, based on the data after the standardization in FIG. 30. First, let the standardized data be area=X1, optical thickness=X2, ..., $\sqrt{\text{(variance)}}$/average=X7, respectively; then f and g as the two principal components indicative of integrated features are calculated based on formulas (2) and (3) below. In the formulas (2) and (3), a1 to a7 and b1 to b7 are coefficients.

$$f = a1*X1 + a2*X2 + \ldots + a7*X7 \qquad (2)$$

$$g = b1*X1 + b2*X2 + \ldots + b7*X7 \qquad (3)$$

At this time, the following conditions are set for the coefficients.

$$a1^2 + a2^2 + \ldots + a7^2 = 1 \qquad (4)$$

$$b1^2 + b2^2 + \ldots + b7^2 = 1 \qquad (5)$$

The reason for setting of the conditions represented by formulas (4) and (5) is that the coefficients a1 to a7, b1 to b7 to maximize the variances of the principal components f, g are calculated in the procedure below and thus the coefficients increase without limit unless the coefficients are limited by the conditions of formulas (4) and (5). "$a1^2 + a2^2 + \ldots + a7^2$" and "$b1^2 + b2^2 + \ldots + b7^2$" correspond to the magnitudes of vectors of the coefficients, and when the magnitudes of the vectors are set to 1, the first principal component f and the second principal component g as new determination axes can be obtained without change in the information amounts of original data.

For making f and g be uncorrelated straight lines orthogonal to each other, the condition below is further set.

$$a1*b1 + a2*b2 + \ldots + a7*b7 = 0 \qquad (6)$$

For making the linear equation reflect the information amounts of original data for f as much as possible, it is conceivable to maximize dispersion of values of the component given by f. Since the dispersion can be considered to be variance, the variance of f is made maximum. When f1, f2, f3, ..., and f43 represent values of f of the respective cells with the number of samples of 43, the variance Vf of f is given by formula (7) below and f satisfying the condition that the variance Vf becomes maximum is calculated.

[Math 1]

$$Vf = \frac{(f_1 - \bar{f})^2 + (f_2 - \bar{f})^2 + (f_3 - \bar{f})^2 + \ldots + (f_{43} - \bar{f})^2}{43} \qquad (7)$$

In the formula (7) above, $$\bar{f} \qquad \text{[Math 2]}$$

is the average of f

By the above method, the coefficients a1, a2, ..., a7 satisfying the condition of above formula (4) and satisfying the condition of above formula (7) are calculated for the first principal component f. FIG. 31 shows the coefficients of the principal component f calculated based on the calculation method described above.

Next, for the second principal component g, the coefficients b1, b2, ..., b7 are calculated so as to satisfy the condition of above formula (5), satisfy the condition of the same spirit as above formula (7) (i.e., the condition to maximize variance), and further satisfy the condition of above formula (6). FIG. 32 shows the coefficients of the second principal component g calculated based on the calculation method described above.

Next, the values of f and g are determined for each cell and they are defined as the first principal component and the second principal component, respectively. FIG. 33 shows the result of calculation of the first principal component f and the second principal component g for each of the cells. (A) in FIG. 33 shows the first principal component f and the second principal component g of the rat pancreatic β cell line (INS-1) and the mouse pancreatic β cell line (MIN-6), and (B) in FIG. 33 shows the first principal component f and the second principal component g of the human pancreatic cancer cell line (MIAPaCa-2) and the human uterine cervix cancer cell line (HeLa).

(Step 4: Plot and Cell Determination)

Figure 34:
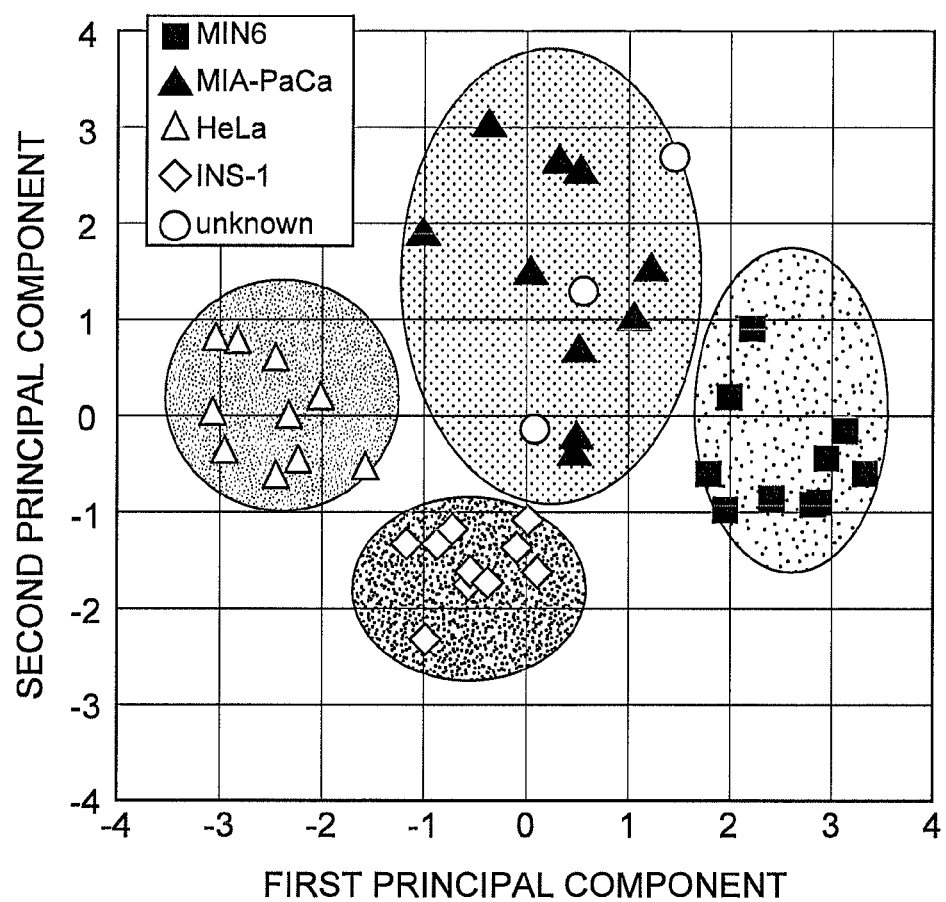
FIG. 34 is a drawing showing the result of plotting of each of cells on a two-component scatter diagram, using values of the first principal component f and the second principal component g, in the sixteenth example.

The analysis unit 207 plots each cell on the two-component scatter diagram, using the values of the first principal component f and the second principal component g shown in FIG. 33, and performs cell determination. FIG. 34 shows the result of the plot, which is an example in which each cell was plotted with the first principal component f on the horizontal axis and the second principal component g on the vertical axis. As seen from the plot result of FIG. 34, the scatter diagram of the first principal component f and the second principal component g (principal component scatter diagram) shows that the four types of cell groups form groups that can be readily discriminated according to their feature values. This indicates that the features of the respective cells can be clearly shown by the calculation to maximize the variance of each principal component (above formula (7)). As a result, it was determined that the unknown cells (unknown represented by ○) on the principal component scatter diagram belonged to the group of MIA-PaCa cells represented by Δ. Since the unknown cells were actually MIA-PaCa, it was confirmed that the cell determination by this experiment was correct.

Example 16 described above is suitably applicable, particularly, to cases where all of many parameters extracted or some of three or more extracted parameters are desired to be effectively used for the cell determination. For example, it is particularly suitable for cases where there are a large number of types of cells to be determined and they are to be determined with high accuracy using the large number of parameters, cases where it is not easy to select two parameters from the large number of extracted parameters, and so on. In Example 16, the principal component analysis is performed on the large number of extracted parameters, whereby the large number of parameters can be made to appropriately affect the cell determination. It is because the principal component analysis uses the two principal components properly reflecting all of the large number of parameters or some of three or more parameters, instead of selecting two out of the large number of extracted parameters, to perform the cell determination.

In the description above, the case where the number of parameters was 7 was described as an example, but, without having to be limited to it, the present example can be applied to cases of three or more parameters. Although description is omitted in order to avoid redundancy, the same experiment as the above experiment was actually conducted with ten parameters and the result obtained was the same as in the case using seven parameters.

LIST OF REFERENCE SIGNS

1, 1A, cell observation device; 10, 10A, 10B, 10C, 10D, 10E, 10F, 10G, 10H image acquisition unit; 20 processing unit; 30 sample; 31 grid; 40, 40A, 40B, 40C screen; 101 cells; 102, 102A, 102B vessel; 103 culture space; 104, 104A, 104D, 104E, 104F objective lens; 105 quantitative phase measurement light source; 105A illumination stop unit; 105D common light source; 106 reflection interference measurement light source; 107, 107A half mirror; 108 dichroic mirror; 109 total reflection mirror; 110 reflection interference detection camera; 111 diffractive interference optical system; 112 quantitative phase detection camera; 113 ring slit; 114 antireflection coat; 115 culture solution; 116 observation window; 117 antireflection coat; 118G optical path for illumination light in quantitative phase measurement; 119G optical path for reference light in quantitative phase measurement; 120G, 122G, 123G lenses; 121G half mirror; 124H illumination wavelength switch device; 125H observation wavelength switch device; 201 image alignment unit; 202 contour extraction unit; 203 contour application unit; 204 first extraction unit; 205 second extraction unit; 206 third extraction unit; 207 analysis unit; 208 reference storage unit.

INDUSTRIAL APPLICABILITY

The present invention provides the cell observation device and the cell observation method capable of obtaining the greater amount of information for appropriate determination and evaluation of the cell state.

The invention claimed is:

1. A cell observation device comprising:
a reflection interference measurement light source;
a quantitative phase measurement light source;
a reflection interference imaging unit which images light emitted from the reflection interference measurement light source and reflected from a cell, to generate a reflection interference image;
a quantitative phase imaging unit which images light emitted from the quantitative phase measurement light source and transmitted by the cell, to generate a quantitative phase image;
an image alignment unit which matches a spatial position of the reflection interference image with a spatial position of the quantitative phase image, thereby to implement alignment between the two images;
a first extraction unit which extracts a first parameter from the reflection interference image in the alignment with the quantitative phase image by the image alignment unit; and
a second extraction unit which extracts a second parameter from the quantitative phase image in the alignment with the reflection interference image by the image alignment unit.

2. The cell observation device according to claim 1, further comprising:
a contour extraction unit which extracts a contour of the cell, based on the quantitative phase image;
a contour application unit which applies the contour extracted by the contour extraction unit, to the reflection interference image to generate a reflection interference image after contour application; and
a third extraction unit which extracts a third parameter from the reflection interference image after contour application.

3. The cell observation device according to claim 1, wherein the first parameter is information based on an adhesion state between a substrate on which the cell is laid, and the cell.

4. The cell observation device according to claim 1, wherein the second parameter is information based on an optical thickness, area, volume of the cell, or a change in refractive index in the cell.

5. The cell observation device according to claim 2, wherein the third parameter is information based on an adhesion state to a substrate, in the contour of the cell.

6. The cell observation device according to any one of claims 1 to 5 claim 1, further comprising:
a reference storage unit which stores as reference data a parameter preliminarily extracted for the cell of a known type or state; and
an analysis unit which determines a type or state of an unknown cell, based on the reference data.

7. The cell observation device according to any one of claims 1 to 5 claim 1, further comprising:
an analysis unit which selects a predetermined parameter from parameters extracted for an unknown cell and which determines a type or state of the unknown cell, using the predetermined parameter selected.

8. The cell observation device according to any one of claim 1, further comprising:
an analysis unit which, when the first extraction unit or the second extraction unit extracts three or more parameters, performs a principal component analysis on said three or more parameters, thereby to determine a type or state of an unknown cell.

9. The cell observation device according to claim 1, wherein low-coherent light is used as the quantitative phase measurement light source.

10. The cell observation device according to claim 1, wherein low-coherent light is used as the reflection interference measurement light source.

11. The cell observation device according to claim 1, further comprising:
an objective lens which condenses the light emitted from the reflection interference measurement light source and reflected from the cell; and
a slit of a ring shape at a position conjugate with an aperture stop on the reflection interference measurement light source side of the objective lens.

12. The cell observation device according to claim 1, further comprising:
a vessel which houses the cell,
wherein an antireflection coat is laid on a side of the vessel opposite to an adhesion face of the cell.

13. The cell observation device according to claim 1, further comprising:
a mirror located between the reflection interference measurement light source and the reflection interference imaging unit and between the quantitative phase measurement light source and the reflection interference imaging unit and having variable ratios of reflection to transmission depending upon wavelengths.

14. A cell observation method comprising:
a reflection interference imaging step wherein a reflection interference imaging unit images light emitted from a reflection interference measurement light source and reflected from a cell, to generate a reflection interference image;
a quantitative phase imaging step wherein a quantitative phase imaging unit images light emitted from a quantitative phase measurement light source and transmitted by the cell, to generate a quantitative phase image;
an image alignment step wherein an image alignment unit matches a spatial position of the reflection interference image with a spatial position of the quantitative phase image, thereby to implement alignment between the two images;
a first extraction step wherein a first extraction unit extracts a first parameter from the reflection interference image in the alignment with the quantitative phase image by the image alignment unit; and
a second extraction step wherein a second extraction unit extracts a second parameter from the quantitative phase image in the alignment with the reflection interference image by the image alignment unit.

15. The cell observation method according to claim 14, further comprising:
a contour extraction step wherein a contour extraction unit extracts a contour of the cell, based on the quantitative phase image;
a contour application step wherein a contour application unit applies the contour extracted by the contour extraction unit, to the reflection interference image, to generate a reflection interference image after contour application; and
a third extraction step wherein a third extraction unit extracts a third parameter from the reflection interference image after contour application.

* * * * *